(12) United States Patent
Choi et al.

(10) Patent No.: US 11,564,656 B2
(45) Date of Patent: Jan. 31, 2023

(54) GENERALIZED INTERLACED SCANNING WITH AN ULTRASOUND PROBE

(71) Applicant: Verathon Inc., Bothell, WA (US)

(72) Inventors: Joon Hwan Choi, Bothell, WA (US); Fuxing Yang, Bothell, WA (US)

(73) Assignee: Verathon Inc., Bothell, WA (US)

( * ) Notice: Subject to any disclaimer, the term of this patent is extended or adjusted under 35 U.S.C. 154(b) by 305 days.

(21) Appl. No.: 16/287,118

(22) Filed: Feb. 27, 2019

(65) Prior Publication Data

US 2019/0282206 A1 Sep. 19, 2019

Related U.S. Application Data

(60) Provisional application No. 62/642,193, filed on Mar. 13, 2018.

(51) Int. Cl.
*A61B 8/00* (2006.01)
*A61B 8/08* (2006.01)

(52) U.S. Cl.
CPC .......... *A61B 8/4461* (2013.01); *A61B 8/4466* (2013.01); *A61B 8/4472* (2013.01); *A61B 8/483* (2013.01); *A61B 8/486* (2013.01); *A61B 8/488* (2013.01); *A61B 8/5207* (2013.01); *A61B 8/5276* (2013.01); *A61B 8/54* (2013.01); *A61B 8/08* (2013.01); *A61B 8/4427* (2013.01); *A61B 8/4433* (2013.01)

(58) Field of Classification Search
CPC ... A61B 8/4461; A61B 8/4466; A61B 8/4472; A61B 8/5207; A61B 8/4427; A61B 8/4433; A61B 8/483
See application file for complete search history.

(56) References Cited

U.S. PATENT DOCUMENTS 3,509,341 A * 4/1970 Hindel ................. G01T 1/1644
250/363.02
4,034,744 A * 7/1977 Goldberg ................. A61B 8/00
600/445

(Continued)

OTHER PUBLICATIONS

PCT International Search Report and Written Opinion issued for the corresponding international application No. PCT/US2019/019800, dated Jun. 14, 2019, 12 pages.

*Primary Examiner* — Joel Lamprecht
*Assistant Examiner* — Nyrobi Celestine
(74) *Attorney, Agent, or Firm* — Snyder, Clark, Lesch & Chung, LLP

(57) ABSTRACT

A system includes an ultrasound probe comprising an ultrasound transducer, a first motor configured to rotate the ultrasound transducer around a horizontal axis to scan a plane, and a second motor configured to rotate the ultrasound transducer around a vertical axis to move to a different plane. The system further includes a controller unit configured to select a number of scan planes for an interlacing scan to scan a volume of an area of interest in a patient's body using the ultrasound probe; select an interlacing factor for the interlacing scan; divide the scan planes into groups of scan planes based on the interlacing factor; and perform the interlacing scan by controlling the first motor and the second motor, wherein the first motor moves in a first direction for at least some of the scan planes and in a second direction for other ones of the scan planes.

20 Claims, 30 Drawing Sheets

| | | FIRST VOLUME | | | | | | | | | | | SECOND VOLUME | | | |
|---|---|---|---|---|---|---|---|---|---|---|---|---|---|---|---|---|
| SCANNING ORDER (610) | 1 | 2 | 3 | 4 | 5 | 6 | 7 | 8 | 9 | 10 | 11 | 12 | 13 | 14 | 15 | ••• |
| PLANE NUMBER (620) | 1 | 3 | 5 | 7 | 9 | 11 | 12 | 10 | 8 | 6 | 4 | 2 | 1 | 3 | 5 | ••• |
| PHI MOTOR DIRECTION (630) | FW | BW | FW | BW | FW | BW | FW | BW | FW | BW | FW | BW | FW | BW | FW | ••• |
| THETA MOTOR DIRECTION (640) | FW | | | | | | BW | | | | | | FW | | | ••• |

601

(56) References Cited

U.S. PATENT DOCUMENTS

| | | | |
|---|---|---|---|
| 4,257,256 A * | 3/1981 | Yoshikawa | A61B 8/14 |
| | | | 73/626 |
| 4,271,706 A | 6/1981 | Ledley | |
| 4,282,879 A | 8/1981 | Kunii et al. | |
| 4,307,421 A | 12/1981 | Smit | |
| 4,341,120 A | 7/1982 | Anderson | |
| 4,375,818 A | 3/1983 | Suwaki et al. | |
| 4,637,256 A | 6/1987 | Sugiyama et al. | |
| 4,841,979 A | 6/1989 | Dow et al. | |
| 4,913,158 A | 4/1990 | Kikuchi et al. | |
| 5,152,294 A | 10/1992 | Mochizuki et al. | |
| 5,181,514 A | 1/1993 | Solomon et al. | |
| 5,487,388 A | 1/1996 | Rello et al. | |
| 5,562,095 A | 10/1996 | Downey et al. | |
| 5,589,870 A | 12/1996 | Curry et al. | |
| 5,740,804 A * | 4/1998 | Cerofolini | A61B 8/12 |
| | | | 600/459 |
| 6,080,108 A | 6/2000 | Dunham | |
| 6,544,175 B1 | 4/2003 | Newman | |
| 6,551,245 B1 | 4/2003 | Irioka et al. | |
| 6,645,151 B2 | 11/2003 | Irioka et al. | |
| 6,709,394 B2 * | 3/2004 | Frisa | G01S 7/52063 |
| | | | 128/916 |
| 6,709,397 B2 | 3/2004 | Taylor | |
| 6,733,457 B2 | 5/2004 | Flesch et al. | |
| 6,780,153 B2 | 8/2004 | Angelsen et al. | |
| 7,066,889 B2 | 6/2006 | Taylor | |
| 7,128,711 B2 | 10/2006 | Medan et al. | |
| 7,881,774 B2 * | 2/2011 | Kobayashi | G01S 15/8993 |
| | | | 600/428 |
| 8,137,279 B2 | 3/2012 | Taylor | |
| 8,403,854 B2 * | 3/2013 | Sasaki | A61B 8/483 |
| | | | 600/443 |
| 8,652,047 B2 * | 2/2014 | Kim | A61B 8/4461 |
| | | | 600/438 |
| 9,386,964 B2 * | 7/2016 | Bagge | G01S 7/52074 |
| 9,408,591 B2 * | 8/2016 | Kotaki | A61B 8/5207 |
| 9,629,608 B2 * | 4/2017 | Imamura | A61B 8/145 |
| 9,924,923 B2 * | 3/2018 | Mauldin, Jr. | A61B 8/5207 |
| 10,231,703 B2 * | 3/2019 | Fearnot | G10K 11/352 |
| 2007/0197913 A1 | 8/2007 | Kim et al. | |
| 2008/0146932 A1 * | 6/2008 | Chalana | A61B 8/0866 |
| | | | 600/447 |
| 2009/0030326 A1 | 1/2009 | Kim et al. | |
| 2009/0105597 A1 * | 4/2009 | Abraham | A61B 8/08 |
| | | | 600/466 |
| 2011/0137172 A1 | 1/2011 | Kim et al. | |
| 2012/0150036 A1 * | 6/2012 | Buckton | A61B 8/5246 |
| | | | 600/443 |
| 2013/0303913 A1 * | 11/2013 | Tian | G01S 7/52085 |
| | | | 600/447 |
| 2014/0024937 A1 | 1/2014 | Kim et al. | |
| 2014/0194743 A1 | 7/2014 | Havel et al. | |
| 2014/0343422 A1 * | 11/2014 | Waki | A61B 8/483 |
| | | | 600/438 |
| 2015/0216512 A1 * | 8/2015 | Luo | A61B 8/58 |
| | | | 600/437 |
| 2016/0000404 A1 * | 1/2016 | Utsunomiya | G01S 7/52085 |
| | | | 600/443 |
| 2016/0192904 A1 | 7/2016 | Kim et al. | |
| 2017/0311923 A1 * | 11/2017 | Saberi | A61B 8/4488 |

* cited by examiner

FIG. 6A (601)

| SCANNING ORDER (610) | 1 | 2 | 3 | 4 | 5 | 6 | 7 | 8 | 9 | 10 | 11 | 12 | 13 | 14 | 15 | ... |
|---|---|---|---|---|---|---|---|---|---|---|---|---|---|---|---|---|
| PLANE NUMBER (620) | 1 | 3 | 5 | 7 | 9 | 11 | 12 | 10 | 8 | 6 | 4 | 2 | 1 | 3 | 5 | ... |
| PHI MOTOR DIRECTION (630) | FW | BW | FW | BW | FW | BW | FW | BW | FW | BW | FW | BW | FW | BW | FW | ... |
| THETA MOTOR DIRECTION (640) | FW | | | | | | BW | | | | | | FW | | | ... |

Columns 1–12: FIRST VOLUME; Columns 13–15+: SECOND VOLUME

FIG. 6B (602)

| SCANNING ORDER (610) | 1 | 2 | 3 | 4 | 5 | 6 | 7 | 8 | 9 | 10 | 11 | 12 | 13 | 14 | 15 | ... |
|---|---|---|---|---|---|---|---|---|---|---|---|---|---|---|---|---|
| PLANE NUMBER (620) | 1 | 5 | 9 | 10 | 6 | 2 | 3 | 7 | 11 | 12 | 8 | 4 | 1 | 5 | 9 | ... |
| PHI MOTOR DIRECTION (630) | FW | BW | FW | BW | FW | BW | FW | BW | FW | BW | FW | BW | FW | BW | FW | ... |
| THETA MOTOR DIRECTION (640) | FW | | | BW | | | FW | | | BW | | | FW | | | ... |

Columns 1–12: FIRST VOLUME; Columns 13–15+: SECOND VOLUME

FIG. 6C (603)

| SCANNING ORDER (610) | 1 | 2 | 3 | 4 | 5 | 6 | 7 | 8 | 9 | 10 | 11 | 12 | 13 | 14 | 15 | ... |
|---|---|---|---|---|---|---|---|---|---|---|---|---|---|---|---|---|
| PLANE NUMBER (620) | 3 | 7 | 11 | 12 | 8 | 4 | 8 | 12 | 9 | 5 | 1 | 3 | 7 | 11 | | ... |
| PHI MOTOR DIRECTION (630) | FW | BW | FW | BW | FW | BW | FW | BW | FW | BW | FW | BW | FW | BW | FW | ... |
| THETA MOTOR DIRECTION (640) | FW | | | BW | | | FW | | | BW | | | FW | | | ... |

Columns 1–12: FIRST VOLUME; Columns 13–15+: SECOND VOLUME

| SCANNING ORDER (610) | 1 | 2 | 3 | 4 | 5 | 6 | 7 | 8 | 9 | 10 | 11 | 12 | 13 | 14 | 15 | ... |
|---|---|---|---|---|---|---|---|---|---|---|---|---|---|---|---|---|
| PLANE NUMBER (620) | 11 | 9 | 7 | 5 | 3 | 1 | 2 | 4 | 6 | 8 | 10 | 12 | 11 | 9 | 7 | ... |
| PHI MOTOR DIRECTION (630) | BW | BW | BW | BW | BW | FW | FW | FW | FW | FW | FW | FW | BW | BW | BW | ... |
| THETA MOTOR DIRECTION (640) | BW | | | | | | FW | | | | | | BW | | | ... |

{ FIRST VOLUME: columns 1–12 }
{ SECOND VOLUME: columns 13–... }

FIRST VOLUME (720)

SECOND VOLUME (724)

FIRST VOLUME (722)

SECOND VOLUME (726)

| SCANNING ORDER (610) | 1 | 2 | 3 | 4 | 5 | 6 | 7 | 8 | 9 | 10 | 11 | 12 | 13 | 14 | 15 | ... |
|---|---|---|---|---|---|---|---|---|---|---|---|---|---|---|---|---|
| PLANE NUMBER (610) | 1 | 3 | 5 | 7 | 9 | 11 | 2 | 4 | 6 | 8 | 10 | 12 | 1 | 3 | 5 | ... |
| PHI MOTOR DIRECTION (610) | FW | BW | FW | BW | FW | BW | FW | BW | FW | BW | FW | BW | FW | BW | FW | ... |
| THETA MOTOR DIRECTION (610) | FW | | | | | | FW | | | | | | FW | | | |

{1–12: FIRST VOLUME; 13–15…: SECOND VOLUME}

| SCANNING ORDER (610) | 1 | 2 | 3 | 4 | 5 | 6 | 7 | 8 | 9 | 10 | 11 | 12 | 13 | 14 | 15 | ... |
|---|---|---|---|---|---|---|---|---|---|---|---|---|---|---|---|---|
| PLANE NUMBER (610) | 1 | 5 | 9 | 2 | 6 | 10 | 3 | 7 | 11 | 4 | 8 | 12 | 1 | 5 | 9 | ... |
| PHI MOTOR DIRECTION (610) | FW | BW | FW | BW | FW | BW | FW | BW | FW | BW | FW | BW | FW | BW | FW | ... |
| THETA MOTOR DIRECTION (610) | FW | | | FW | | | FW | | | FW | | | FW | | | |

{1–12: FIRST VOLUME; 13–15…: SECOND VOLUME}

GENERALIZED INTERLACED SCANNING WITH AN ULTRASOUND PROBE

PRIORITY INFORMATION

This patent application claims benefit of priority to U.S. Provisional Application No. 62/642,193, entitled "GENERALIZED INTERLACED SCANNING WITH AN ULTRASOUND PROBE" and filed on Mar. 13, 2018, which is hereby incorporated herein by reference in its entirety.

BACKGROUND INFORMATION

An ultrasound probe may generate ultrasound signals using a transducer, such as, for example, a piezoelectric transducer or a capacitive transducer, which converts electrical signals into ultrasound energy and which converts ultrasound echoes back into electrical signals. Ultrasound probes are typically used to identify a target organ or other structures in the body and/or determine features associated with the target organ/structure, such as the size of the organ/structure or the volume of fluid in the organ. In order for an ultrasound to properly scan a target organ/structure, the ultrasound probe may need to perform scans in multiple planes to generate a volume scan. Performing scans in multiple planes may present various challenges.

BRIEF DESCRIPTION OF THE DRAWINGS

FIGS. 6A, 6B, 6C, and 6D are diagrams of exemplary scanning order tables according to an implementation described herein;

FIGS. 14A and 14B are diagrams of exemplary scanning order tables with continuous theta motor movement according to an implementation described herein.

DETAILED DESCRIPTION OF PREFERRED EMBODIMENTS

Figure 1A:
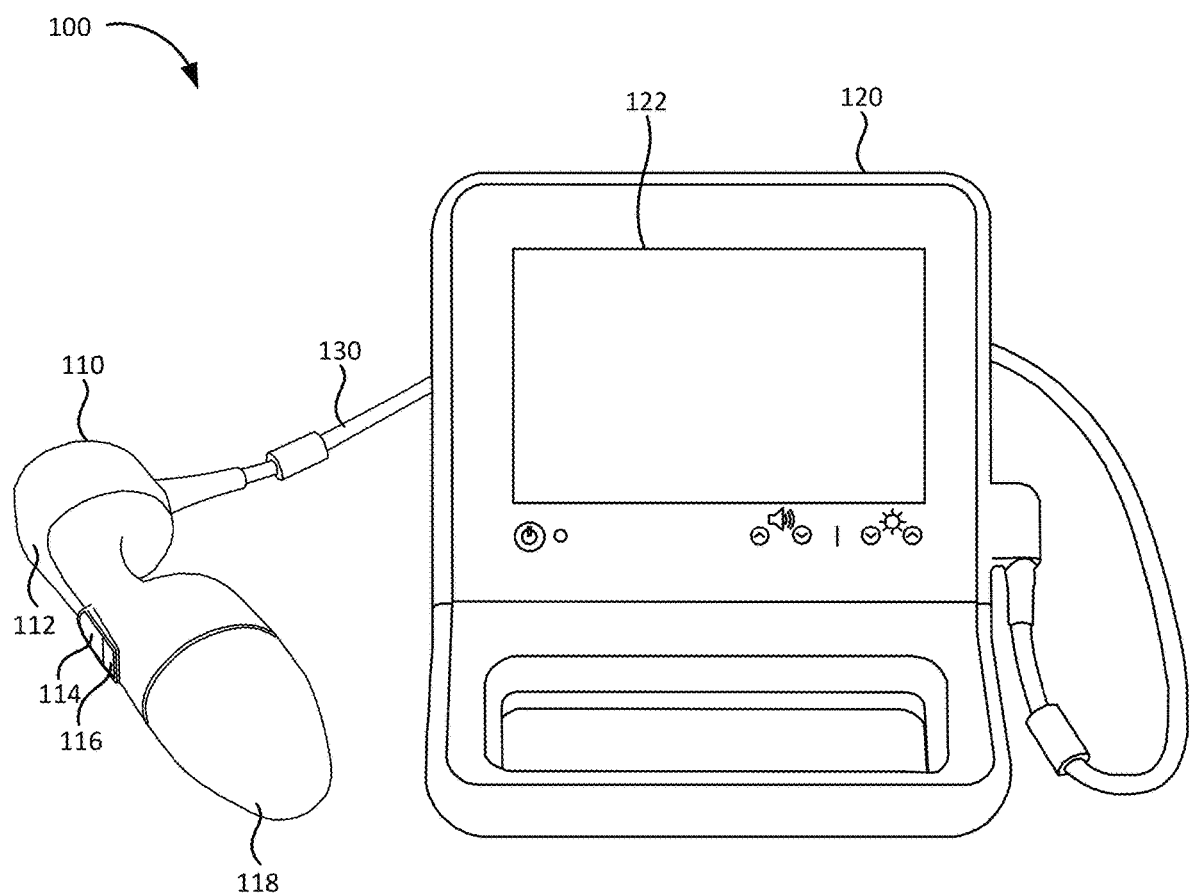
FIG. 1A is a diagram illustrating an exemplary ultrasound system according to an implementation described herein.

The following detailed description refers to the accompanying drawings. The same reference numbers in different drawings identify the same or similar elements.

An ultrasound probe may be positioned on a patient's body to perform a volume scan (e.g., a three-dimensional (3D) scan) of an area of interest, such as a body organ, joint, blood vessel, and/or another type of area of a patient's body. A volume scan may include a set of ultrasound images captured in different planes transecting the area of interest. For example, a volume scan may include planar ultrasound images taken at particular angular intervals in a circle around a center of the area of interest.

The ultrasound probe may include a single element ultrasound transducer. The ultrasound probe may include a first motor, referred to herein as a "phi" motor, configured to rotate around a horizontal axis to move the ultrasound transducer along a sector of a particular ultrasound imaging plane to scan the plane. The ultrasound probe may further include a second motor, referred to herein as a "theta" motor, configured to rotate around a vertical axis to move the ultrasound transducer to a different ultrasound imaging plane. Thus, a volume scan may be performed by moving the theta motor to a first plane, moving the phi motor to sweep out a sector of the first plane, moving the theta motor to a second plane, moving the phi motor to sweep out a sector of the second plane, moving the theta motor to a third plane, and so on until all the planes are scanned to complete one volume scan.

A volume scan may be performed with theta homing. In theta homing, the theta motor returns to the initial theta motor position after a volume scan is completed, in order to start the next volume scan. A volume scan may also be performed with phi homing. In phi homing, the phi motor only performs scans in one direction. Thus, in phi homing, the phi motor returns back to an initial position after scanning a plane and the theta motor needs to wait for the phi motor to return before moving to the next plane. Theta homing and phi homing slow down scanning and reduce image quality. For example, theta homing may produce a large delay between consecutive volume scans and phi homing may increase the amount of time required to perform each individual volume scan. Furthermore, such slow volume scan rates may produce significant motion blur and reduce image quality.

Implementations described herein relate to generalized interlaced scanning with an ultrasound probe. The interlaced scanning may include interlaced theta motor motion and bi-directional phi motor motion. The interlaced scanning may be performed without theta homing and without phi homing and generates a smooth continuous volume scan without homing delay, improved volume scan rate, and reduced motion blur.

An interlaced scan may be defined by a number of scan planes. For example, the scan planes may be distributed around a circle and separated by angles corresponding to 180° divided by the number of scan planes. The interlaced scan may further be defined by an interlacing factor k and the scan planes may be divided into k groups. The interlaced scan may follow a set of rules. The rules may include that the phi motor changes direction every plane, that the theta motor changes directions with every group of planes, and that the theta motor does not change directions within a group of planes. Furthermore, since no theta homing is performed, a first volume scan may be performed with the theta motor starting in a particular plane and followed by a second volume scan with the theta motor starting in a different plane.

An ultrasound system may be configured to select a number of scan planes for an interlacing scan to scan a volume of an area of interest in a patient's body using an ultrasound transducer, select an interlacing factor for the interlacing scan, divide the scan planes into groups of scan planes based on the interlacing factor, and perform the interlacing scan by controlling a phi motor to scan a plane and a theta motor to move to a different plane, wherein the phi motor moves in a forward direction for at least some of the scan planes and in a backward direction for other ones of the scan planes. Furthermore, the theta motor may move in a forward direction for at least some of the groups of scan planes and in a backward direction for other ones of the groups of scan planes.

Furthermore, dividing the scan planes into groups of scan planes based on the interlacing factor may include sequentially numbering the scan planes, dividing the scan planes into a number of groups of scan planes corresponding to the interlacing factor, and sequentially distributing the numbered scan planes into the groups of scan planes.

Furthermore, performing the interlacing scan may include scanning a particular plane by moving the phi motor in a direction that is opposite to the direction the phi motor moved when scanning the previous plane; moving to a next plane by moving the theta motor by a number of planes corresponding to the interlacing factor, wherein the direction of the theta motor changes if the next plane is in a different group than the previously scanned plane.

In some implementations, an ultrasound probe may include a one-dimensional (1D) linear or curved array of ultrasound transducers and a theta motor, instead of a single ultrasound transducer with a theta motor and a phi motor. In such implementations, movement of the phi motor to scan a plane may be replaced by electronically controlling the 1D array of ultrasound transducers to scan a plane. Thus, in such implementations, performing an interlacing scan may include controlling the 1D array of ultrasound transducers to scan a plane and controlling a motor configured to rotate the 1D array of ultrasound transducers around a vertical axis to move to a different plane, with the motor changing directions for every group of scan planes without changing directions within a group of scan planes. For example, the interlacing scan may include scanning a particular plane by electronically controlling the 1D array of transducers, moving to a next plane by moving the theta motor a number of planes corresponding to the interlacing factor, wherein the direction of the theta motor changes if the next plane is in a different group than the previously scanned plane A particular implementation may include an interlacing scan with two scan planes and with the interlacing factor k being set to two. Such an implementation may result in continuous bi-plane scanning.

Implementations described herein further relate to overlapping the motion of the phi motor and the theta motor. The arc of movement of a phi motor may include a region of acceleration, a region of constant speed, and a region of deceleration. Ultrasound image data collection may be performed within the region of constant speed while the theta motor remains still. However, since no data collection is performed during the acceleration or deceleration of the phi motor, movement of the theta motor during the time that the phi motor is accelerating or decelerating may improve the volume scan rate by reducing delays from phi motor acceleration/deceleration and/or theta motor movement. Thus, performing an interlacing scan may include controlling the theta motor to rotate while the phi motor is in the acceleration or deceleration region of the range of motion of the phi motor. For example, the theta motor may move from a first plane to a second plane while the phi motor is in the acceleration or deceleration region of the range of motion.

Implementations described herein further relate to continuous theta motor movement. An ultrasound probe may include wiring, such as wiring to an ultrasound transducer. The wiring may limit the range of motion of the theta motor. For example, the wiring may prevent the theta motor from continuously rotating in one direction, as such rotation may cause the wiring to wrap around a spindle attaching the ultrasound transducer to a base or may cause the wiring to break. An ultrasound probe may be configured to enable continuous theta motor movement. In some implementations, the wiring may be replaced with an electrically conducting slip ring. In other implementations, the wiring may be replaced with a wireless communication connection to the ultrasound transducer, such as a Bluetooth connection, a Bluetooth Low Energy connection, a Near Field Communication (NFC) connection, and/or another type of short-range wireless communication connection. Thus, performing an interlacing scan may include controlling the theta motor to move in a same direction for all the groups of scan planes.

FIG. 1A is a diagram illustrating an exemplary ultrasound system 100 according to an implementation described herein. As shown in FIG. 1A, ultrasound system 100 may include an ultrasound probe 110, a base unit 120, and a cable 130.

Ultrasound probe 110 may house one or more ultrasound transducers configured to generate ultrasound energy at a particular frequency and/or pulse repetition rate and to receive reflected ultrasound energy (e.g., ultrasound echoes) and convert the reflected ultrasound energy into electrical signals. For example, in some implementations, ultrasound probe 110 may be configured to transmit ultrasound signals in a range that extends from approximately about two megahertz (MHz) to approximately 10 or more MHz (e.g., 18 MHz). In other implementations, ultrasound probe 110 may be configured to transmit ultrasound signals in a different range. Furthermore, ultrasound probe 110 may house one or more motors for controlling the movement of the ultrasound transducer.

Ultrasound probe 110 may include a handle 112, a trigger 114, and a dome 118 (also referred to as a "nose"). A user (e.g., a medical practitioner, etc.) may hold ultrasound probe 110 via handle 112 and press trigger 114 to activate one or more ultrasound transceivers and transducers located in dome 118 to transmit ultrasound signals toward a patient's area of interest (e.g., a particular body organ, a body joint, a blood vessel, etc.). For example, probe 110 may be positioned on a pelvic area of a patient and over the patient's bladder.

Handle 112 enables a user to move probe 110 relative to a patient's area of interest. Activation of trigger 114 initiates an ultrasound scan of a selected anatomical portion while dome 118 is in contact with a surface portion of a patient's body when the patient's area of interest is scanned. In some implementations, trigger 114 may include a toggle switch 116. Toggle switch 116 may be used to toggle between different aiming planes during an aiming mode of ultrasound system 100.

Dome 118 may enclose one or more ultrasound transducers and may be formed from a material that provides an appropriate acoustical impedance match to the anatomical portion and/or permits ultrasound energy to be properly focused as it is projected into the anatomical portion. Dome 118 may also include transceiver circuitry that includes a transmitter and a receiver to transmit and receive ultrasound signals. Probe 110 may communicate with base unit 120 via a wired connection, such as via cable 130. In other implementations, probe 110 may communicate with base unit 120 via a wireless connection (e.g., Bluetooth, WiFi, etc.).

Base unit 120 may house and include one or more processors or processing logic configured to process reflected ultrasound energy that is received by probe 110 to produce an image of the scanned anatomical region. Furthermore, base unit 120 may include display 122 to enable a user to view images from an ultrasound scan, and/or to enable operational interaction with respect to the user during operation of probe 110. For example, display 122 may include an output display/screen, such as a liquid crystal display (LCD), light emitting diode (LED) based display, touchscreen, and/or another type of display that provides text and/or image data to a user.

For example, display 122 may provide instructions for positioning probe 110 relative to a selected anatomical portion of a patient. Alternatively, ultrasound probe 110 may include a small display (e.g., in handle 112) that provides instructions for positioning ultrasound probe 110. Display 122 may also display two-dimensional or three-dimensional images of the selected anatomical region. In some implementations, display 122 may include a graphical user interface (GUI) that allows the user to select various features associated with an ultrasound scan. For example, display 122 may include selection items (e.g., buttons, dropdown menu items, checkboxes, etc.) to select one or more parameters for performing an interlaced volume scan, such as the number of planes and/or the interlacing factor. Furthermore, display 122 may include selection items to select particular types of ultrasound images to be obtained, such as B-mode ultrasound images, probability mode (P-mode) ultrasound images, Doppler mode ultrasound images, harmonic mode ultrasound images, M-mode ultrasound images, and/or other types of ultrasound images.

Figure 1B:
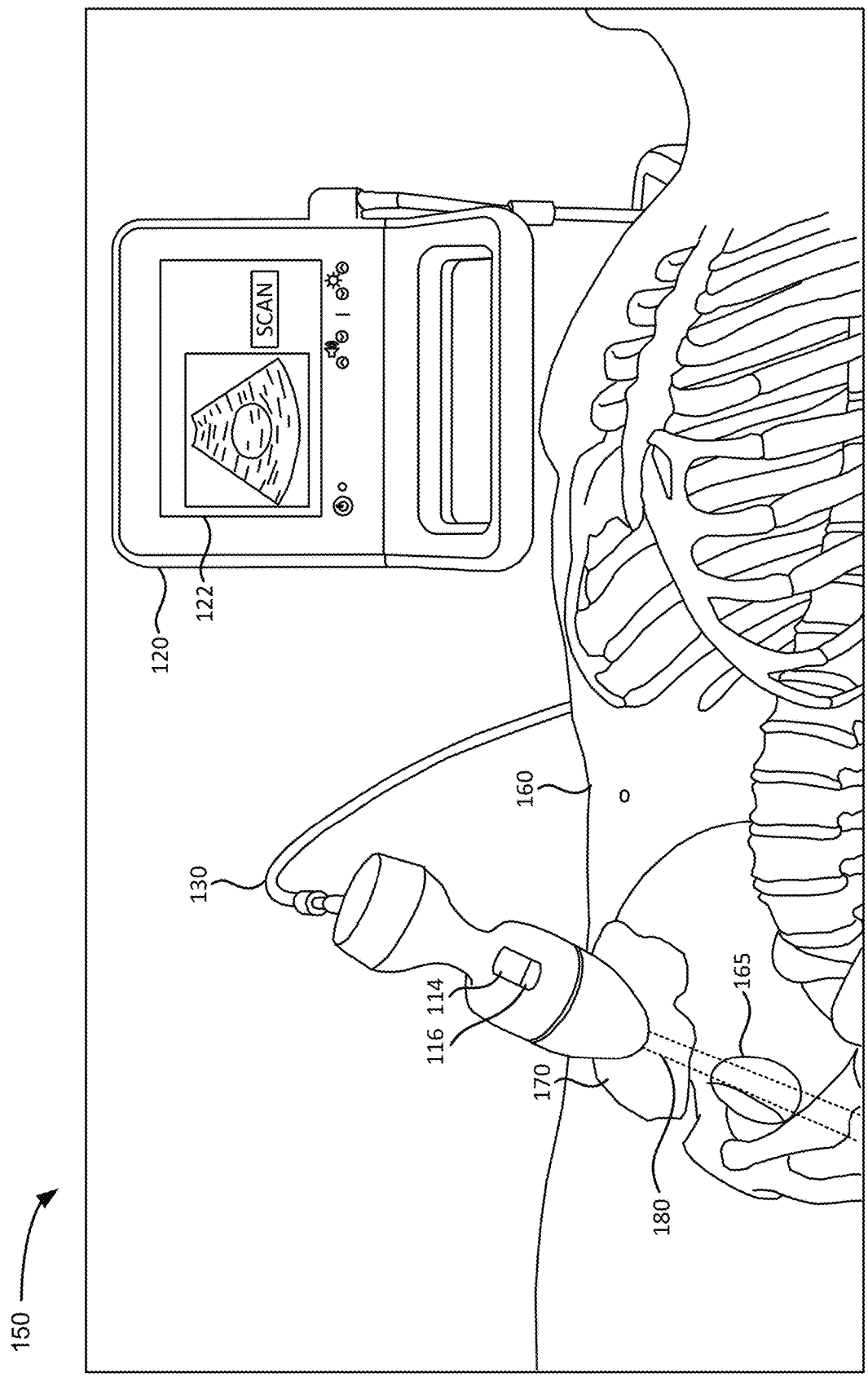
FIG. 1B is a diagram illustrating an exemplary environment for the ultrasound system of FIG. 1A according to an implementation described herein.

FIG. 1B is a diagram illustrating an exemplary environment 150 for ultrasound system 100 according to an implementation described herein. Environment 150 illustrates the operation of ultrasound system 100 with respect to a patient 160. As shown in FIG. 1B, patient 160 may be positioned so that a patient's area of interest may be scanned. For example, assume the area of interest corresponds to the patient's bladder 165. To scan bladder 165, ultrasound probe 110 may be positioned against a surface portion of patient 160 that is proximate to the anatomical portion to be scanned. The user may apply acoustic gel 170 (or gel pads) to the skin of patient 160 over the area of bladder 165 to provide an acoustical impedance match when dome 118 is placed against the skin. The user may select to perform a volume scan of bladder 165 by pressing trigger 114, by pressing a scan button on display 122, by speaking a voice command, and/or using another type of scan activation technique. In response, ultrasound probe 110 may transmit ultrasound signals 180 through bladder 165 and may receive reflected ultrasound signals. The reflected ultrasound signals may be processed into images that are displayed on display 122.

Although FIGS. 1A and 1B show exemplary components of ultrasound system 100, in other implementations, ultrasound system 100 may include fewer components, different components, additional components, or differently arranged components than depicted in FIGS. 1A and 1B. Additionally or alternatively, one or more components of ultrasound system 100 may perform one or more tasks described as being performed by one or more other components of ultrasound system 100.

For example, in other embodiments, ultrasound probe 110 may correspond to a self-contained device that includes a microprocessor housed within ultrasound probe 110, configured to operably control the one or more ultrasound transducers, and to process the reflected ultrasound energy to generate ultrasound images. Accordingly, a display on ultrasound probe 110 may be used to display the generated images and/or to view other information associated with the operation of ultrasound probe 110. In yet other implementations, ultrasound probe 110 may be coupled to a general-purpose computer, such as a laptop, tablet, and/or a desktop computer (via a wired or wireless connection) that includes software that at least partially controls the operation of ultrasound probe 110 and/or that includes software to process information received from ultrasound probe 110 to generate ultrasound images.

Figure 2A:
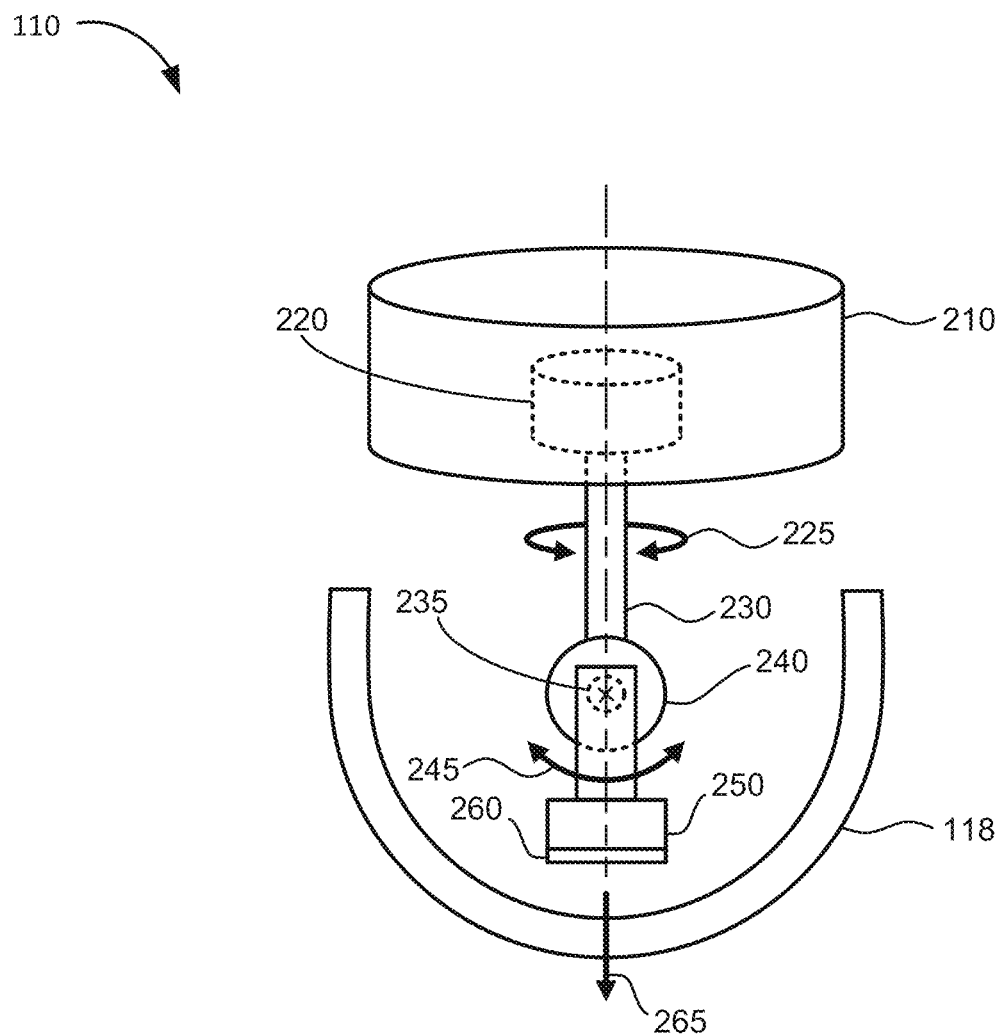
FIG. 2A is a diagram of a first exemplary ultrasound probe according to an implementation described herein.

FIG. 2A is a diagram of a first exemplary implementation of ultrasound probe 110 according to an implementation described herein. As shown in FIG. 2A, ultrasound probe 110 may include a single transducer element coupled to two rotational motors. In this implementation, ultrasound probe 110 may include a base 210 connected to dome 118, a theta motor 220, a spindle 230, a phi motor 240, and a transducer bucket 250 with a transducer 260. Theta motor 220, phi motor 240, and/or transducer 260 may include wired or wireless electrical connections that electrically connect theta motor 220, phi motor 240, and/or transducer 260 to base unit 120 via cable 130 (not shown in FIG. 2A).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in a longitudinal direction with respect to transducer 260, by rotating around a vertical axis referred to herein as a theta (θ) rotational plane 225. Spindle 230 may terminate in a shaft 235 and phi motor 240 may be mounted onto shaft 235. Phi motor 240 may rotate around an axis orthogonal to the theta rotational plane 225 around a horizontal axis referred to herein as a phi (φ) rotational plane 245. Transducer bucket 250 may be mounted to phi motor 240 and may move with phi motor 240.

Transducer 260 may be mounted to transducer bucket 250. Transducer 260 may include a piezoelectric transducer, a capacitive transducer, and/or another type of ultrasound transducer. Transducer 260, along with transceiver circuitry associated with transducer 260, converts electrical signals to ultrasound signals at a particular ultrasound frequency or range of ultrasound frequencies, receives reflected ultrasound signals (e.g., echoes, etc.), and converts the received ultrasound signals to electrical signals. Transducer 260 may transmit and receive ultrasound signals in a signal direction 265 that is substantially perpendicular to the surface of transducer 260.

Signal direction 265 may be controlled by the movement of phi motor 240 and the orientation of phi motor may be controlled by theta motor 220. For example, phi motor 240 may rotate back and forth across an angle that is less than 180 degrees to generate ultrasound image data for a particular plane and theta motor 220 may rotate to particular positions to obtain ultrasound image data for different planes.

In an aiming mode, theta motor 220 may remain stationary while phi motor 240 rotates back and forth to obtain ultrasound image data for a particular aiming plane. In the aiming mode, theta motor 220 may move back and forth between multiple aiming planes and phi motor 240 may rotate back and forth to obtain ultrasound image data. As an example, theta motor 220 may move between two orthogonal planes while the aiming mode is selected. As another example, theta motor 220 may sequentially rotate through three planes at 120 degrees to each other during the aiming mode.

In a 3D scan mode, theta motor 220 may cycle through a set of planes one or more times to obtain a full 3D scan of an area of interest. In each particular plane of the set of planes, phi motor 240 may rotate to obtain ultrasound image data for the particular plane. The movement of theta motor 220 and phi motor 240 may be interlaced in the 3D scan mode. For example, the movement of phi motor 240 in a first direction may be followed by a movement of theta motor 220 from a first plane to a second plane, followed by the movement of phi motor 240 in a second direction opposite to the first direction, followed by movement of theta motor 220 from the second plane to a third plane, etc. Such interlaced movement may enable ultrasound probe 110 to obtain smooth continuous volume scanning as well as improve the rate at which the scan data is obtained.

The ultrasound plane images comprising the 3D scan may include B-mode ultrasound images, P-mode ultrasound images, Doppler mode images (e.g., Power Doppler, Continuous Wave Doppler, Pulsed Wave Doppler, etc.), harmonic mode ultrasound images, motion mode (M-mode) ultrasound images, and/or other types of ultrasound images.

In some implementations, ultrasound probe 110 may be configured to enable continuous movement of theta motor 220. For example, wiring from base 210 to phi motor 240 and/or to ultrasound transducer 260 may limit the movement of theta motor 220 in a particular direction. Thus, theta motor 220 may need to alternate rotating forward and backwards to move ultrasound transducer 260 to particular scan planes to prevent binding or breaking of wires. In some implementations, the wiring may be replaced with an electrical connection that does not limit such movement of theta motor 220 and that enables theta motor 220 to continue to rotate in one direction.

In some implementations, the wiring may be replaced with one or more conductive slip rings on spindle 230 and/or on shaft 235. A conductive slip ring may maintain an electrical connection with two conductive surfaces that maintain contact while rotating around each other. Furthermore, a conductive lubricant may be present between the two conductive surfaces to reduce friction. In other implementations, the wiring may be replaced with one or more wireless connections. For example, base 210 may include a first wireless transceiver and transducer bucket 250 may include a second wireless transducer. The two wireless transducers may exchange wireless signals to control ultrasound transducer 260. The wireless transducers may communicate via a short-range wireless communication method, such as, for example, a Bluetooth connection, a Bluetooth Low Energy connection, an NFC connection, and/or another type of short-range wireless communication method.

Figure 2B:
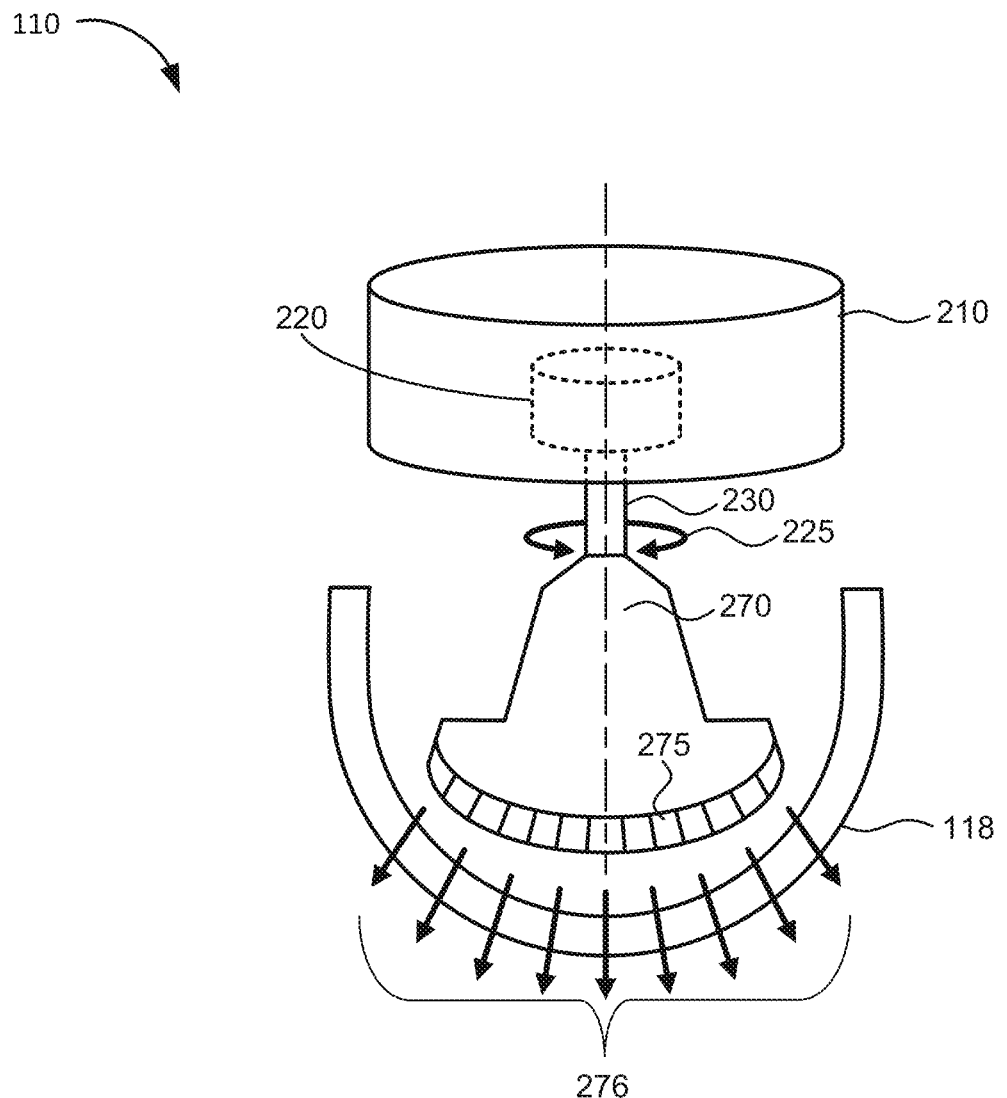
FIG. 2B is a diagram of a second exemplary ultrasound probe according to an implementation described herein.

FIG. 2B is a diagram of a second exemplary implementation of ultrasound probe 110 according to an implementation described herein. As shown in FIG. 2B, ultrasound probe 110 may include a 1D array of transducer elements coupled to a rotation motor. In this implementation, ultrasound probe 110 may include a base 210 connected to dome 118, a theta motor 220, a spindle 230, and a transducer bucket 270 with a 1D transducer array 275. Theta motor 220 and/or 1D transducer array 275 may include wired or wireless electrical connections that electrically connect theta motor 220 and/or 1D transducer array 275 to base unit 120 via cable 130 (not shown in FIG. 2B).

Base 210 may house theta motor 220 and provide structural support to ultrasound probe 110. Base 210 may connect to dome 118 and may form a seal with dome 118 to protect the components of ultrasound probe 110 from the external environment. Theta motor 220 may rotate spindle 230 with respect to base 210 in longitudinal direction with respect to 1D transducer array 275 by rotating around theta rotational plane 225. Spindle 230 may terminate in transducer bucket 270. 1D transducer array 275 may be mounted to transducer bucket 270. 1D transducer array 275 may include a curved or phased 1D array of piezoelectric transducers, capacitive transducers, and/or other types of ultrasound transducers. 1D transducer array 275 may convert electrical signals to ultrasound signals at a particular ultrasound frequency or range of ultrasound frequencies, may receive reflected ultrasound signals (e.g., echoes, etc.), and may convert the received ultrasound signals to electrical signals. One or more elements of 1D transducer array 275 may transmit and receive ultrasound signals in a particular direction of a set of directions, illustrated as item 276 in FIG. 2B. Thus, together, the elements of 1D transducer array 275 may generate ultrasound image data for a particular plane by electronically controlling the elements of 1D transducer array 275.

When performing an interlacing scan using ultrasound probe 110 of FIG. 2B, to scan a particular plane, instead of using phi motor 240, 1D transducer array 275 may be controlled to tilt the ultrasound beam electronically in a phi direction, either by selectively firing a subset of transducers in 1D transducer array 275 or by controlling a firing delay between the individual transducer elements, resulting in 1D transducer array 275 to electronically sweep an ultrasound beam in an arc in either a forward or backward direction. In other implementations, the transducers of 1D transducer array 275 may be fired substantially simultaneously to obtain ultrasound image data for a plane in which 1D transducer array 275 is positioned.

Thus, in a 3D scan mode, theta motor 220 may cycle through a set of planes one or more times to obtain a full 3D scan of an area of interest. In each particular plane of the set of planes, 1D transducer array 275 may obtain ultrasound image data by controlling the transducers of 1D transducer array 275. The movement of theta motor 220 and the firing of 1D transducer array 275 may be interlaced in the 3D scan mode. For example, the firing of 1D transducer array 275 may be followed by a movement of theta motor 220 from a first plane to a second plane, followed by the another firing of 1D transducer array 275, followed by movement of theta motor 220 from the second plane to a third plane, etc. Such interlaced movement may enable ultrasound probe 110 to obtain smooth continuous volume scanning as well as improve the rate at which the scan data is obtained.

In some implementations, ultrasound probe 110 of FIG. 2B may be configured to enable continuous movement of theta motor 220. For example, wiring from base 210 to 1D transducer array 275 may limit the movement of theta motor 220 in a particular direction. Thus, theta motor 220 may need to alternate rotating forward and backwards to move 1D transducer array 275 to particular scan planes to prevent binding or breaking of wires. In some implementations, the wiring may be replaced with an electrical connection that does not limit such movement of theta motor 220 and that enables theta motor 220 to continue to rotate in one direction. Furthermore, in some implementations, the wiring may be replaced with one or more conductive slip rings on spindle 230 and/or on shaft 235, and/or one or more wireless connections, as explained above with reference to FIG. 2A.

Figure 2C:
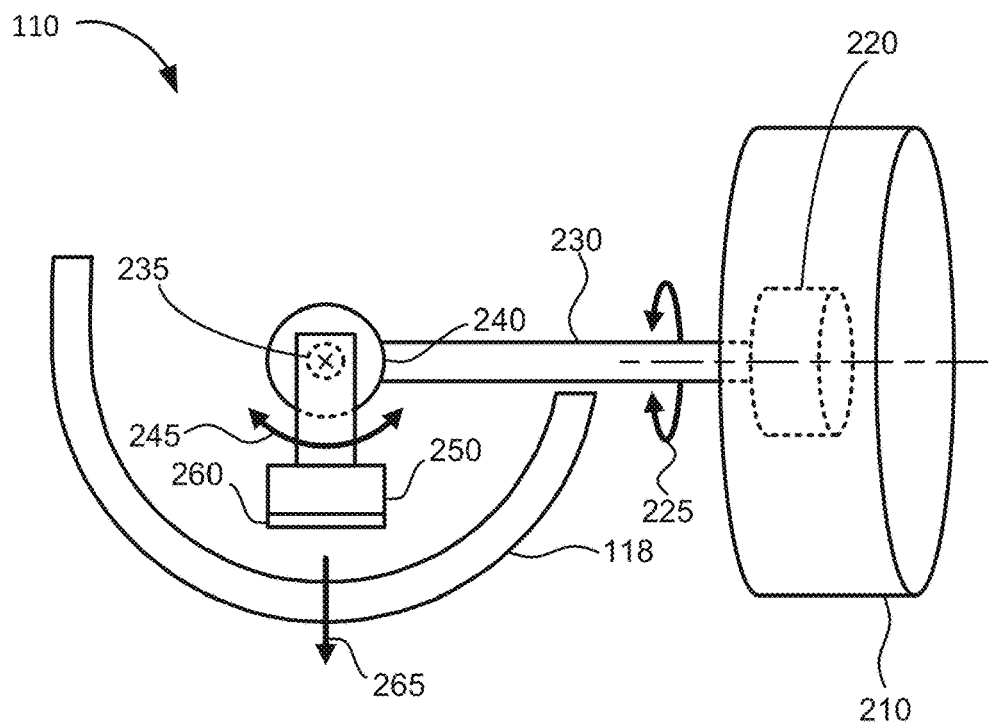
FIG. 2C is a diagram of a third exemplary ultrasound probe according to an implementation described herein.

FIG. 2C is a diagram of a third exemplary implementation of ultrasound probe 110 according to an implementation described herein. As shown in FIG. 2C, ultrasound probe 110 may be configured with spindle 230 positioned perpendicularly to shaft 235 and signal direction 265. As phi motor 240 rotates around the axis of shaft 235, the arrangement of ultrasound probe 110 shown in FIG. 2C may result in theta motor 220 moving the scan planes scanned by phi motor 240 in a rotational plane 225 around spindle 230.

Figure 2D:
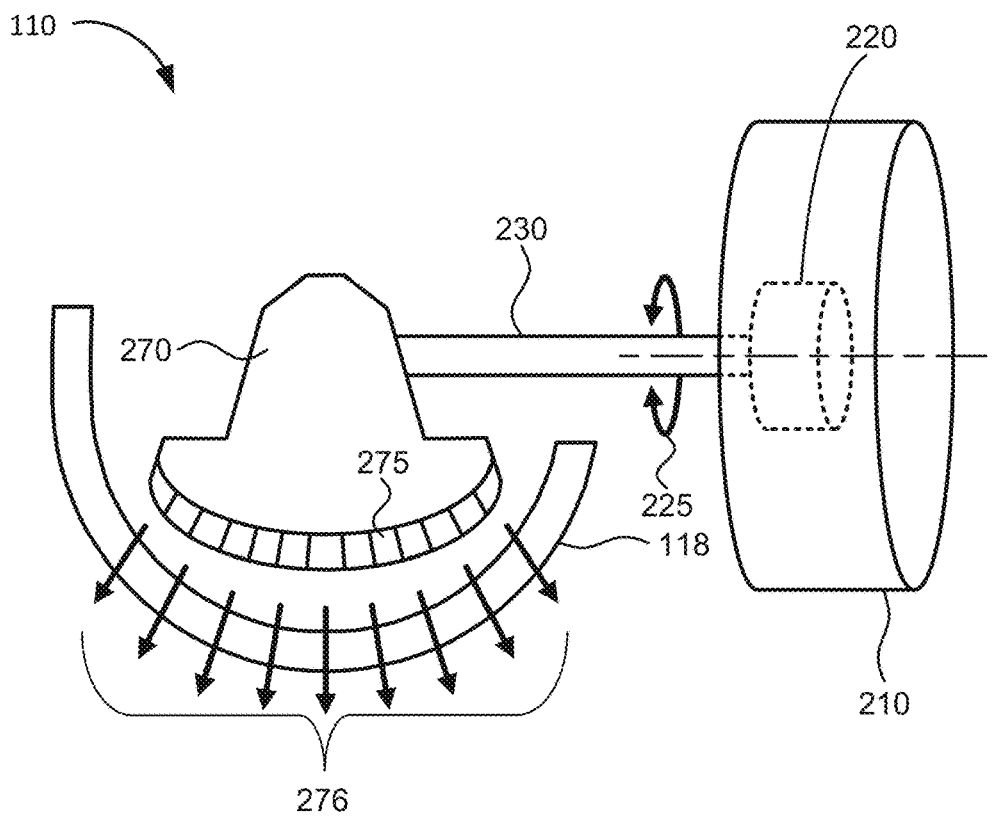
FIG. 2D is a diagram of a fourth exemplary ultrasound probe according to an implementation described herein

FIG. 2D is a diagram of a fourth exemplary implementation of ultrasound probe 110 according to an implementation described herein. As shown in FIG. 2D, ultrasound probe 110 may include transducer bucket 270 and 1D transducer array 275 with spindle 230 positioned perpendicularly to the center of set of directions 276. The arrangement of ultrasound probe 11 shown in FIG. 2D may result in theta motor 220 moving the scan planes scanned by 1D transducer array 275 in a rotational plane 225 around spindle 230. Thus, while in FIGS. 2A and 2B, phi motor 240 rotates around a horizontal axis and theta motor 220 rotates around a vertical axis, in FIGS. 2C and 2D, phi motor 240 rotates around a first horizontal axis, and theta motor 220 rotates around a second horizontal axis that is perpendicular to the first horizontal axis.

Configurations of ultrasound probe 110 shown in FIGS. 2C and 2D enable the execution of a fan scan by moving the scan planes scanned by phi motor 240 along a cylindrical curved surface, as compared with moving the scan planes within a plane (e.g., a horizontal plane) using the configuration of ultrasound probe 110 shown in FIGS. 2A and 2B. A fan scan may be used when the patient's area of interest corresponds to a concave surface (e.g., the front of the neck, the flexing surface of a joint, the lower back, etc.) and/or when the target organ has an elongated shape (e.g., scanning the aorta, the large intestine, etc.). The interlaced scans described herein may also be implemented using the configurations of ultrasound probe 110 shown in FIGS. 2C and 2D.

Although FIGS. 2A and 2B show exemplary components of ultrasound probe 110, in other implementations, ultrasound probe 110 may include fewer components, different components, additional components, or differently arranged components than depicted in FIGS. 2A and 2B. Additionally or alternatively, one or more components of ultrasound probe 110 may perform one or more tasks described as being performed by one or more other components of ultrasound probe 110.

Figure 3:
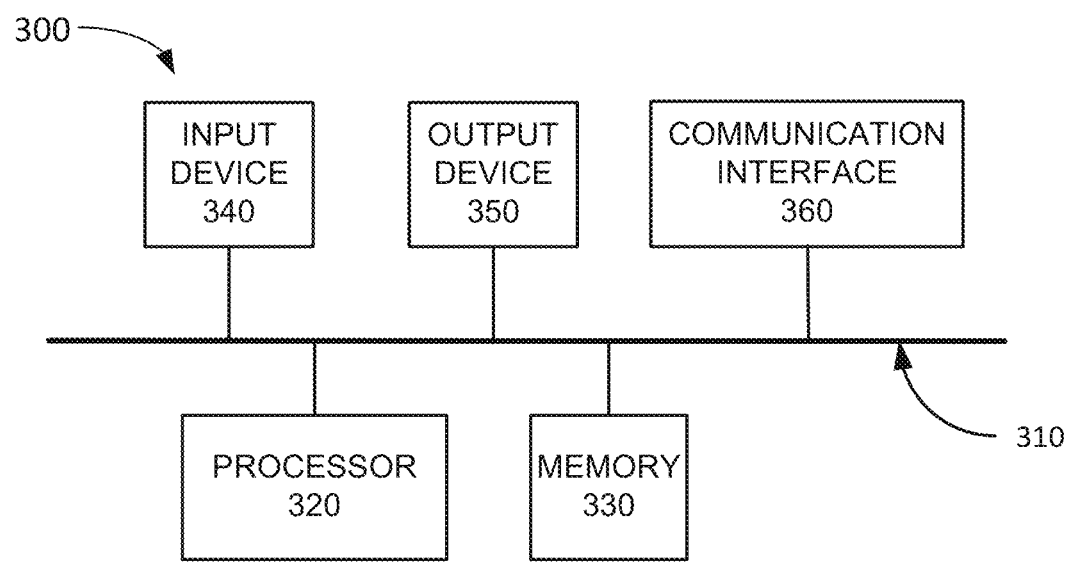
FIG. 3 is a diagram illustrating exemplary components of the controller unit of FIG. 1A.

FIG. 3 is a diagram illustrating example components of a device 300 according to an implementation described herein. Ultrasound probe 110 and/or base unit 120 may each include one or more devices 300. As shown in FIG. 3, device 300 may include a bus 310, a processor 320, a memory 330, an input device 340, an output device 350, and a communication interface 360.

Bus 310 may include a path that permits communication among the components of device 300. Processor 320 may include any type of single-core processor, multi-core processor, microprocessor, latch-based processor, and/or processing logic (or families of processors, microprocessors, and/or processing logics) that interprets and executes instructions. In other embodiments, processor 320 may include an application-specific integrated circuit (ASIC), a field-programmable gate array (FPGA), and/or another type of integrated circuit or processing logic.

Memory 330 may include any type of dynamic storage device that may store information and/or instructions, for execution by processor 320, and/or any type of non-volatile storage device that may store information for use by processor 320. For example, memory 330 may include a random access memory (RAM) or another type of dynamic storage device, a read-only memory (ROM) device or another type of static storage device, a content addressable memory (CAM), a magnetic and/or optical recording memory device and its corresponding drive (e.g., a hard disk drive, optical drive, etc.), and/or a removable form of memory, such as a flash memory.

Input device 340 may allow an operator to input information into device 300. Input device 340 may include, for example, a keyboard, a mouse, a pen, a microphone, a remote control, an audio capture device, an image and/or video capture device, a touch-screen display, and/or another type of input device. In some embodiments, device 300 may be managed remotely and may not include input device 340. In other words, device 300 may be "headless" and may not include a keyboard, for example.

Output device 350 may output information to an operator of device 300. Output device 350 may include a display, a printer, a speaker, and/or another type of output device. For example, device 300 may include a display, which may include a liquid-crystal display (LCD) for displaying content to the customer. In some embodiments, device 300 may be managed remotely and may not include output device 350. In other words, device 300 may be "headless" and may not include a display, for example.

Communication interface 360 may include a transceiver that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. Communication interface 360 may include a transmitter that converts baseband signals to radio frequency (RF) signals and/or a receiver that converts RF signals to baseband signals. Communication interface 360 may be coupled to an antenna for transmitting and receiving RF signals.

Communication interface 360 may include a logical component that includes input and/or output ports, input and/or output systems, and/or other input and output components that facilitate the transmission of data to other devices. For example, communication interface 360 may include a network interface card (e.g., Ethernet card) for wired communications and/or a wireless network interface (e.g., a WiFi) card for wireless communications. Communication interface 360 may also include a universal serial bus (USB) port for communications over a cable, a Bluetooth™ wireless interface, a radio-frequency identification (RFID) interface, a near-field communications (NFC) wireless interface, and/or any other type of interface that converts data from one form to another form.

As will be described in detail below, device 300 may perform certain operations relating to performing an interlaced scan. Device 300 may perform these operations in response to processor 320 executing software instructions contained in a computer-readable medium, such as memory 330. A computer-readable medium may be defined as a non-transitory memory device. A memory device may be implemented within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of, or in combination with, software instructions to implement processes described herein. Thus, implementations described herein are not limited to any specific combination of hardware circuitry and software.

Although FIG. 3 shows exemplary components of device 300, in other implementations, device 300 may include fewer components, different components, additional components, or differently arranged components than depicted in FIG. 3. Additionally or alternatively, one or more components of device 300 may perform one or more tasks described as being performed by one or more other components of device 300.

Figure 4:
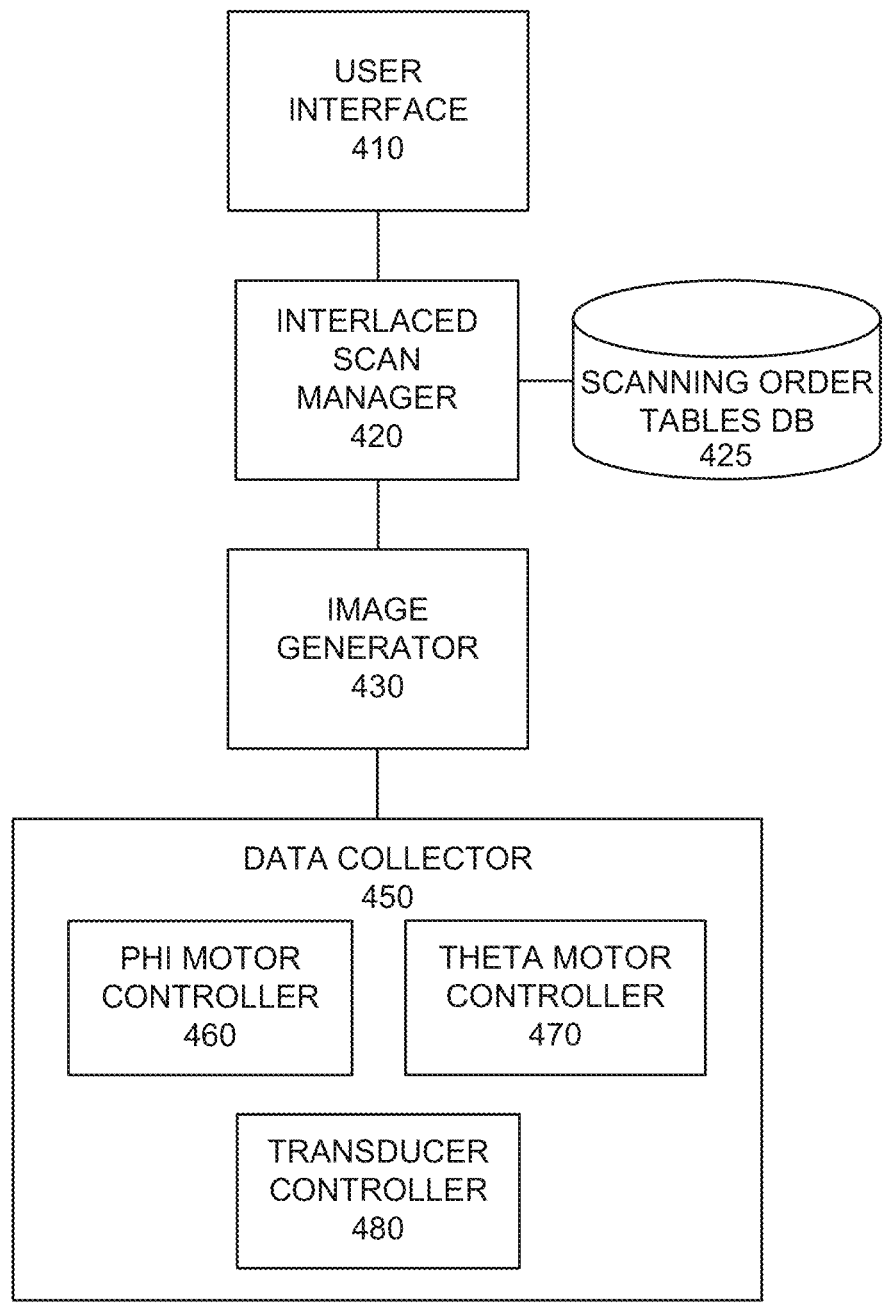
FIG. 4 is a diagram illustrating exemplary functional components of the system of FIG. 1A.

FIG. 4 is a diagram illustrating exemplary functional components of ultrasound system 100. The functional components of ultrasound system 100 may be implemented, for example, via processor 320 executing instructions from memory 330. Alternatively, some or all of the functional components of ultrasound system 100 may be implemented via hard-wired circuitry. As shown in FIG. 4, ultrasound system 100 may include a user interface 410, an interlaced scan manager 420, a scanning order tables database (DB) 425, an image generator 430, and a data collector 450.

User interface 410 may generate a user interface (e.g., a graphical user interface) that displays ultrasound images to a user via display 122 and that is configured to receive selections and/or commands from the user via a touchscreen associated with display 122, via one or more control keys located on base unit 120 and/or on ultrasound probe 110, via a microphone included in base unit 120, and/or via another type of input method. For example, a user may select a type of ultrasound image, an aiming mode via user interface 410, may select one or more aiming mode planes, and/or may select to perform a 3D scan once the user is satisfied with the position of ultrasound probe 110 during an aiming mode.

Interlaced scan manager 420 may generate a 3D scan for an area of interest in a patient's body. For example, in response to a user selecting to perform the 3D scan, interlaced scan manager 420 may instruct image generator 430 to generate ultrasound images for a particular set of planes in a particular sequence with an interlaced movement of theta motor 220 and phi motor 240 based on information stored in scanning order tables DB 425. Scanning order tables DB 425 may store one or more scanning order tables. A particular scanning order table may include, for a particular number of planes and a particular interlacing factor k, information identifying a scanning order for a set of planes and a corresponding movement direction for theta motor 220 and phi motor 240 for each plane. In some implementations, a particular scanning order table may be selected by a user. In other implementations, a particular scanning order table may be selected based on one or more scan parameters. Exemplary scanning order tables are described below with reference to FIGS. 6A, 6B, and 6C.

Furthermore, interlaced scan manager 420 may be configured to enable a user to select, and then to perform, particular types of interlaced scans. For example, interlaced scan manager 420 may select and perform a continuous bi-plane scanning, to perform scanning with overlap of phi motor and theta motor movement (e.g., moving theta motor 220 from a first plane to a second pane while phi motor 240 is in the acceleration or deceleration region of its range of motion), to perform continuous theta motor movement in one direction, and/or other types of interlaced scans.

Image generator 430 may generate ultrasound images in particular planes. For example, image generator 430 may instruct data collector to obtain a particular type of ultrasound image, to move to a particular plane (e.g., a particular position of theta motor 220), and to generate an ultrasound image of a particular type for the particular plane (e.g., using phi motor 240 and transducer 260).

Data collector 450 may be configured to collect ultrasound image data from ultrasound probe 110. Data collector 450 may include a phi motor controller 460, a theta motor controller 470, and a transducer controller 480. Phi motor controller 460 may control phi motor 240. Theta motor controller 470 may control theta motor 220. Transducer controller 480 may control transducer 260.

Although FIG. 4 shows exemplary components of ultrasound system 100, in other implementations, ultrasound system 100 may include fewer components, different components, additional components, or differently arranged components than depicted in FIG. 4. Additionally or alternatively, one or more components of ultrasound system 100 may perform one or more tasks described as being performed by one or more other components of ultrasound system 100.

Figure 5:
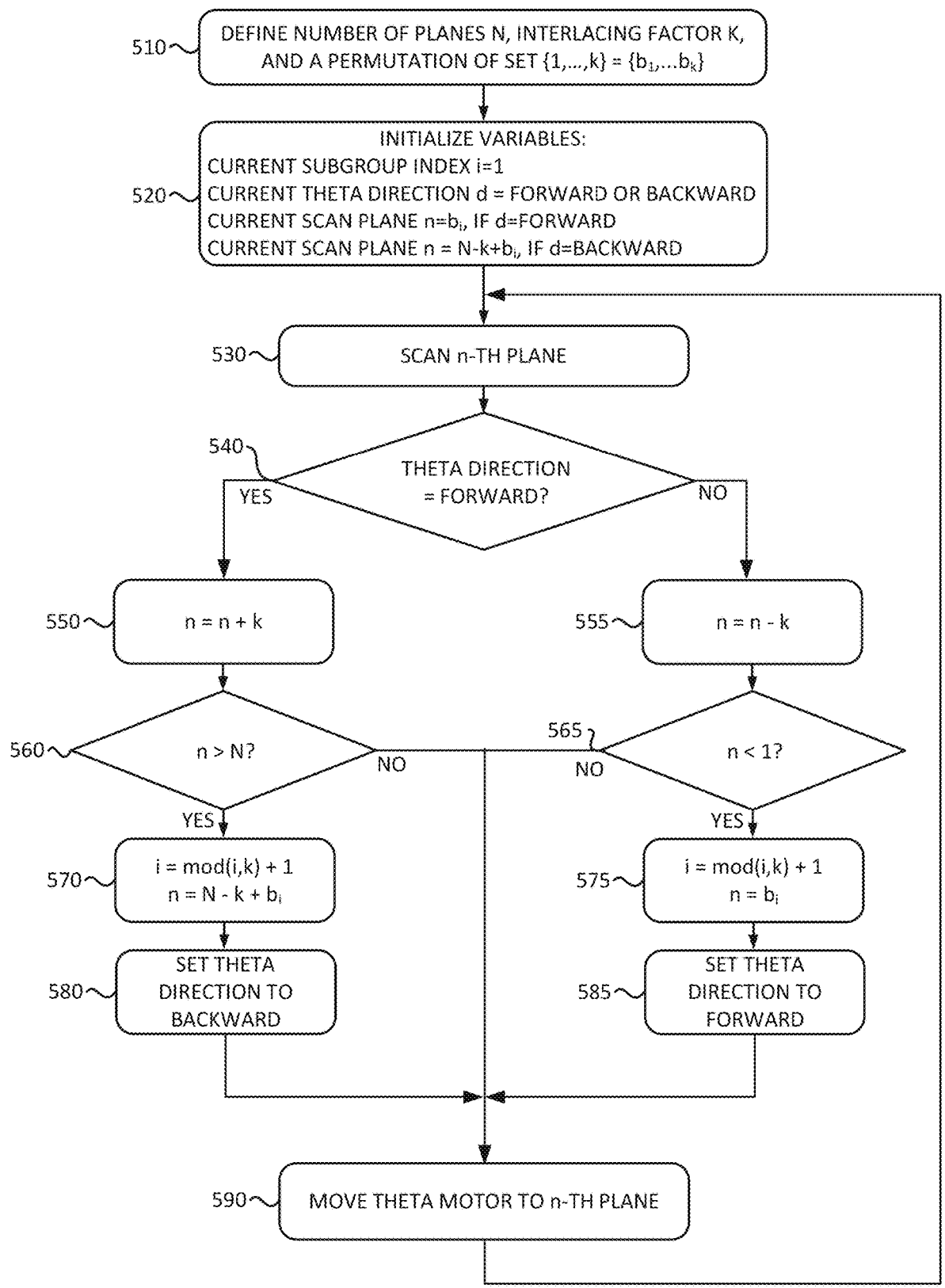
FIG. 5 is a flowchart of a process for interlaced scanning according to an implementation described herein.

FIG. 5 is a flowchart of a process for interlaced scanning according to an implementation described herein. In some implementations, the process of FIG. 5 may be performed by ultrasound system 100. In other implementations, some or all of the process of FIG. 5 may be performed by another device or a group of devices separate from ultrasound system 100.

The process of FIG. 5 may include defining a number of planes N, an interlacing factor k, and a permutation set $\{b_1, \ldots, b_k\}$ of the set of integers $\{1, \ldots, k\}$ (block 510). The interlacing factor k may determine the number of groups of scan planes and the permutation set may define a sequence in which the groups of scan planes are scanned. Thus, $b_i$ refers to the i-th group of scan planes. For example, if there are N=12 planes, with an interlacing factor k=4, the planes are divided into 4 groups by assigning the numbered planes sequentially into 4 groups: Group 1=\{1,5,9\}, Group 2=\{2,6,10\}, Group 3=\{3,7,11\}, and Group 4=\{4,8,12\}. As an example, choosing a permutation set of $\{b_1,b_2,b_3,b_4\}=\{3, 2,4,1\}$ results in a scanning plane order of (3→7→11)→(10→6→2)→(4→8→12)→(9→5→1), in which the scanning direction alternates between forward and backward direction between sequential groups. As another example, choosing a permutation set of $\{b_1,b_2,b_3,b_4\}=\{1,2,3,4\}$ results in a scanning plane order of $(1\to5\to9)\to(10\to6\to2)\to(3\to7\to11)\to(12\to8\to4)$.

In some implementations, a user may select the number of planes N, the interlacing factor k, and the permutation set $\{b_1, \ldots, b_k\}$ from a list of options displayed on display 122 when an interlacing scan is selected. In other implementations, ultrasound system 100 may automatically select a particular number of scan planes, interlacing factor, and/or permutation set based on one or more parameters associated with a scan to be performed, such as the area of interest, image size, type of ultrasound images selected, and/or another type of parameter.

The variables may be initialized (block 520). In particular, the current index i may be set to 1, the current theta motor direction d may be set to either forward or backward, and the current scan plane n may be set to $b_1$ if theta motor direction d is set to "forward", and to $N-k+b_i$ if theta motor direction d is set to "backward". In some implementations, a "forward" direction for theta motor 220 may be defined as moving along a circle in the direction of increasing plane numbers and a "backward" direction may be defined as moving along the circle in the direction of decreasing plane numbers. In other implementations, "forward" and "backward" directions for theta motor 220 may be defined differently. For example, "forward" for theta motor 220 may be defined as counterclockwise and "backward" for theta motor 220 may be defined as clockwise.

Furthermore, in some implementations, "forward" for phi motor 240 may be defined as moving along a plane from the position along the circle at which the plane is numbered and "backward" for phi motor 240 may be defined as moving along a plane toward the position along the circle at which the plane is numbered. In other implementations, "forward" and "backward" directions for phi motor 240 may be defined differently. For example, "forward" for phi motor 240 may be defined as clockwise and "backward" for theta motor 220 may be defined as counterclockwise.

The n-th plane may then be scanned (block 530). Transducer 260 or 1D transducer array 275 may perform a B-mode ultrasound scan, a P-mode ultrasound scan, a Doppler mode ultrasound scan, a harmonic mode ultrasound scan, and/or another type of ultrasound scan of the n-th plane. As an example, in implementations that use ultrasound probe 110 of FIG. 2A, the n-th plane may be scanned by moving phi motor 240 in a direction that is opposite to the direction phi motor 240 moved in when scanning the previous plane. Thus, if phi motor 240 moved in a forward direction for the previous plane, phi motor 240 may move in a backward direction, and if phi motor 240 moved in a backward direction for the previous plane, phi motor 240 may move in a forward direction. When scanning the first plane, phi motor 240 may move in a default first direction (e.g., forward in some implementation, backward in other implementations, etc.).

As another example, in implementations that use ultrasound probe 110 of FIG. 2B, the n-th plane may be scanned by electronically controlling the transducers of 1D transducer array 275 to scan the n-the by firing the transducers in a particular sequence. As yet another example, the transducers of 1D transducer array 275 may be fired without a time delay by firing the transducers substantially simultaneously or in a random order.

A determination may be made as to whether the current theta direction is set to forward (block 540). If the current theta direction is set to forward (block 540—YES), n may be set to n+k (block 550). In other words, the current scan plane may be increased by the interlacing factor. A determination may be made as to whether n is set to a number greater than N, which corresponds to the total number of scan planes (block 560). If n>N (block 560—YES), the current index i may be set to mod(i,k)+1 and n may be set to $N-k+b_i$ (block 570), and the theta motor direction may be set to backward (block 580). Theta motor 220 may then be moved to the n-th scan plane (block 590) and processing may return to block 530 to scan the n-th scan plane by moving phi motor 240 in the direction that is opposite to the last direction phi motor 240 moved in (or by electronically controlling 1D transducer array 275 to scan the n-th plane). Returning to block 560, If n≤N (block 560—NO), processing may proceed to block 590 to move the theta motor 220 to the n-th scan plane and processing may return to block 530 to scan the n-th scan plane by moving phi motor 240 in the direction that is opposite to the last direction phi motor 240 moved in (or by electronically controlling 1D transducer array 275 to scan the n-th plane).

Returning to block 540, if the current theta direction is set to backwards (block 540—NO), n may be set to n–k (block 555). In other words, the current scan plane may be decreased by the interlacing factor. A determination may be made as to whether n is set to less than 1 (block 565). If n<1 (block 565—YES), the current index i may be set to mod(i,k)+1 and n may be set to $b_1$ (block 575), and the theta motor direction may be set to forward (block 585). Theta motor 220 may then be moved to the n-th scan plane (block 590) and processing may return to block 530 to scan the n-th scan plane by moving phi motor 240 in the direction that is opposite to the last direction phi motor 240 moved in (or by electronically controlling 1D transducer array 275 to scan the n-th plane). Returning to block 565, If n≥1 (block 565—NO), processing may proceed to block 590 to move the theta motor 220 to the n-th scan plane and processing may return to block 530 to scan the n-th scan plane by moving phi motor 240 in the direction that is opposite to the last direction phi motor 240 moved in (or by electronically controlling 1D transducer array 275 to scan the n-th plane).

The process of FIG. 5 may continue until a user selects to stop performing volume scan, until a selected number of volume scans have been performed, and/or until a different type of trigger condition is satisfied.

FIGS. 6A, 6B, 6C, and 6D are diagrams of exemplary scanning order tables. FIG. 6A illustrates a scanning order table 601 for an interlacing scan with 12 planes and an interlacing factor k of 2. Scanning order table 601 may include a scanning order row 610, a plane number row 620, a phi motor direction row 630, and a theta motor direction row 640. Scanning order row 610 may include information identifying the order in which the planes are scanned. Plane number row 620 may include information identifying the plane number based on a sequential numbering of the planes from a starting plane around a circle (see, for example, FIG. 7A). Phi motor direction row 630 may include information identifying the movement direction of phi motor 240 for each plane ("FW" corresponds to forward motion with respect to the plane numbering and "BW" corresponds to backward motion with respect to the plane numbering). Theta motor direction row 640 may include information identifying the movement direction of theta motor 220 for each group of planes.

As shown in FIG. 6A, the scanning order of the planes for one volume scan for an interlacing scan for 12 planes and an interlacing factor of 2, and a permutation set of {1,2} is 1, 3, 5, 7, 9, 11, followed by 12, 10, 8, 6, 4, 2. The direction of phi motor 240 changes with each plane and the direction of theta motor 220 changes with each group of planes. Since the interlacing factor is 2, the number of groups of planes is 2.

FIG. 6B illustrates a scanning order table 602 for an interlacing scan with 12 planes, an interlacing factor k of 4, and a permutation set of {1,2,3,4}. As shown in FIG. 6B, the scanning order of the planes for one volume scan for an interlacing scan for 12 planes and an interlacing factor of 4, is 1, 5, 9, followed by 10, 6, 2, followed by 3, 7, 11, and followed by 12, 8, 4. The direction of phi motor 240 changes with each plane and the direction of theta motor 220 changes with each group of planes. Since the interlacing factor is 4, the number of groups of planes is 4.

FIG. 6C illustrates a scanning order table 603 for another interlacing scan with 12 planes and an interlacing factor k of 4, and a permutation set of {3, 2, 4, 1}. As shown in FIG. 6C, the scanning order for scanning order table 603 for one volume scan is 3, 7, 11, followed by 10, 6, 2, followed by 4, 8, 12, followed by 9, 5, 1. Scanning order table 603 differs from scanning order table 602 by having a different permutation set.

FIG. 6D illustrates a scanning order table 604 for an interlacing scan with 12 planes an interlacing factor k of 2, and a permutation set of {2, 1}. As shown in FIG. 6D, the scanning order for scanning order table 604 is 11, 9, 7, 5, 3, 1, followed by 2, 4, 6, 8, 10, and 12. Scanning order table 604 differs from scanning order table 601 by having a different permutation set and illustrates that theta motor direction row 640 does not need to start with a "forward" direction.

Figure 7A:
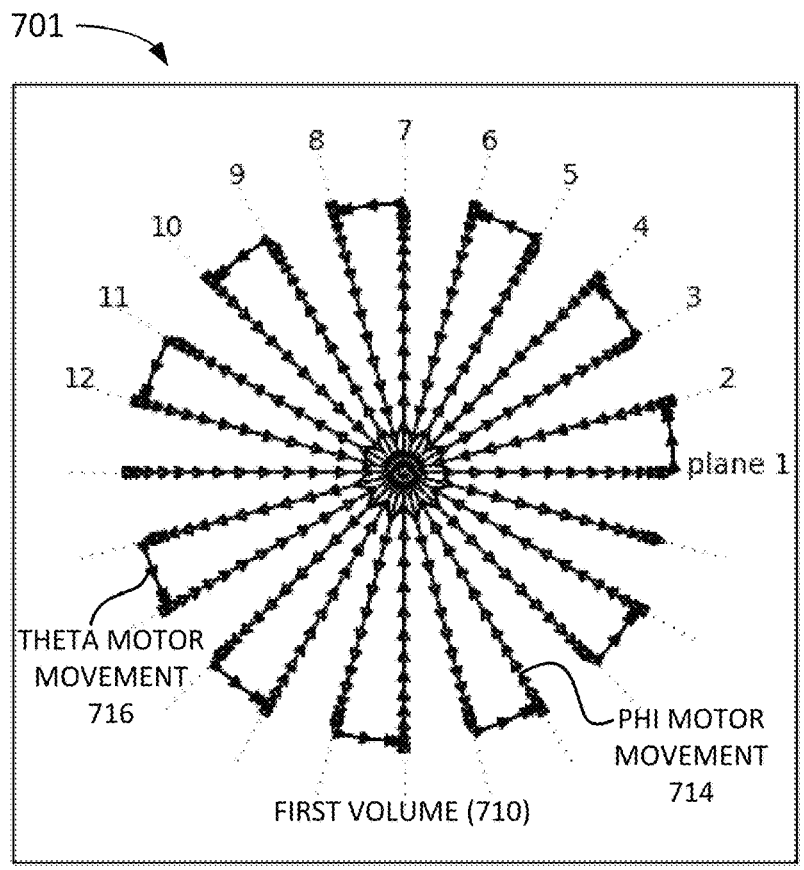
FIGS. 7A, 7B, 7C, and 7D are diagrams of exemplary ultrasound transducer trajectories for volume scans based on 12 planes according to an implementation described herein.
Figure 7A:
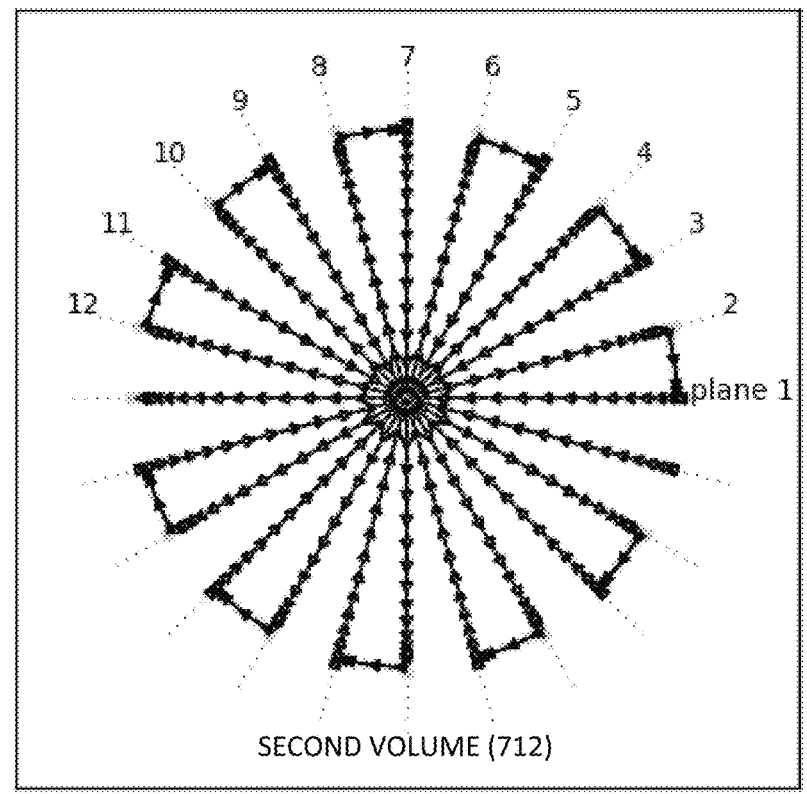

FIGS. 7A, 7B, 7C, and 7D are diagrams of exemplary ultrasound transducer trajectories for volume scans based on 12 planes. FIG. 7A illustrates a trajectory 701 of ultrasound transducer 260 for an interlaced scan based on 12 planes and an interlacing factor of one for a first volume scan 710 and a second volume scan 712. FIG. 7A identifies phi motor movement 714 for plane 9 to demonstrate that phi motor 240 moves across particular planes and theta motor movement 716 from plane 2 to plane 3 to demonstrate that theta motor 220 moves from plane to plane.

Figure 7B:
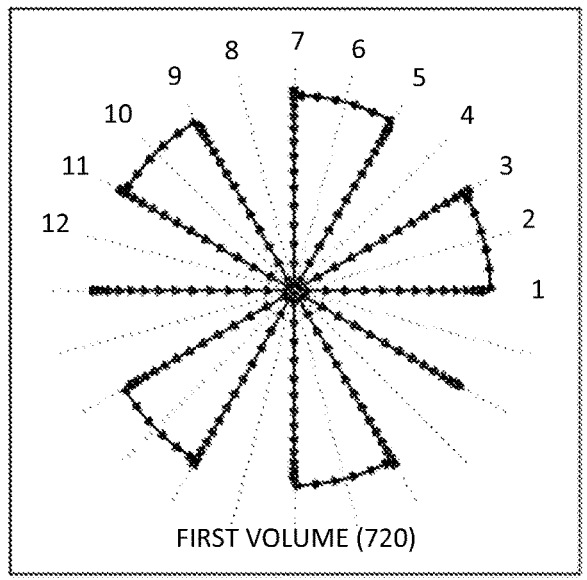
Figure 7B:
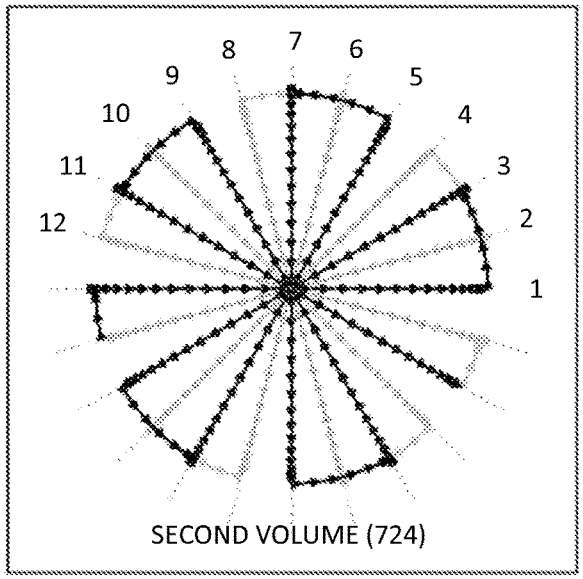
Figure 7B:
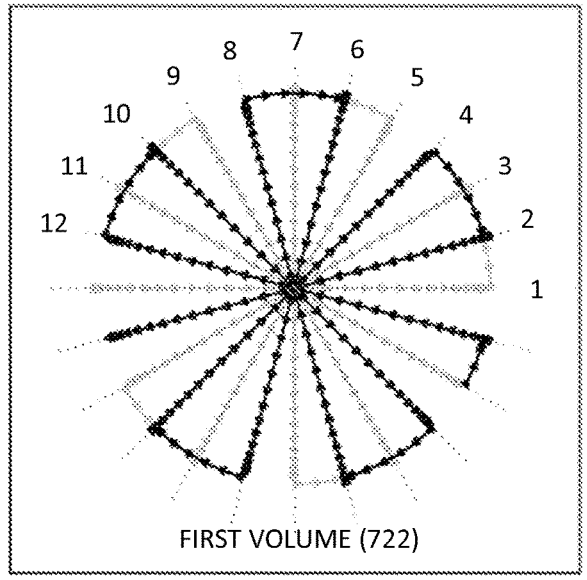
Figure 7B:
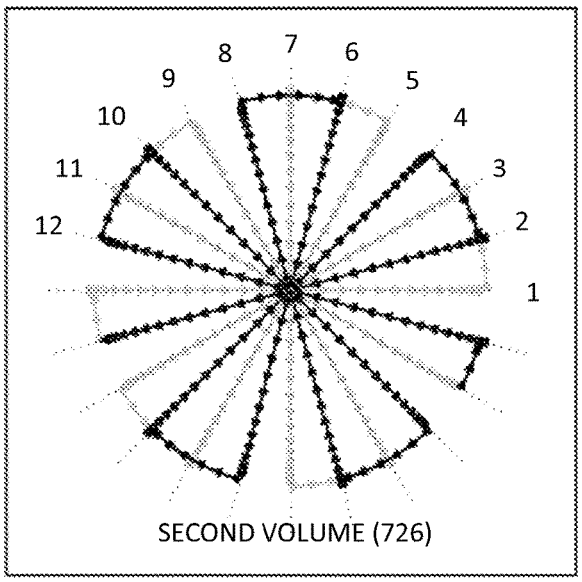
Figure 7C:
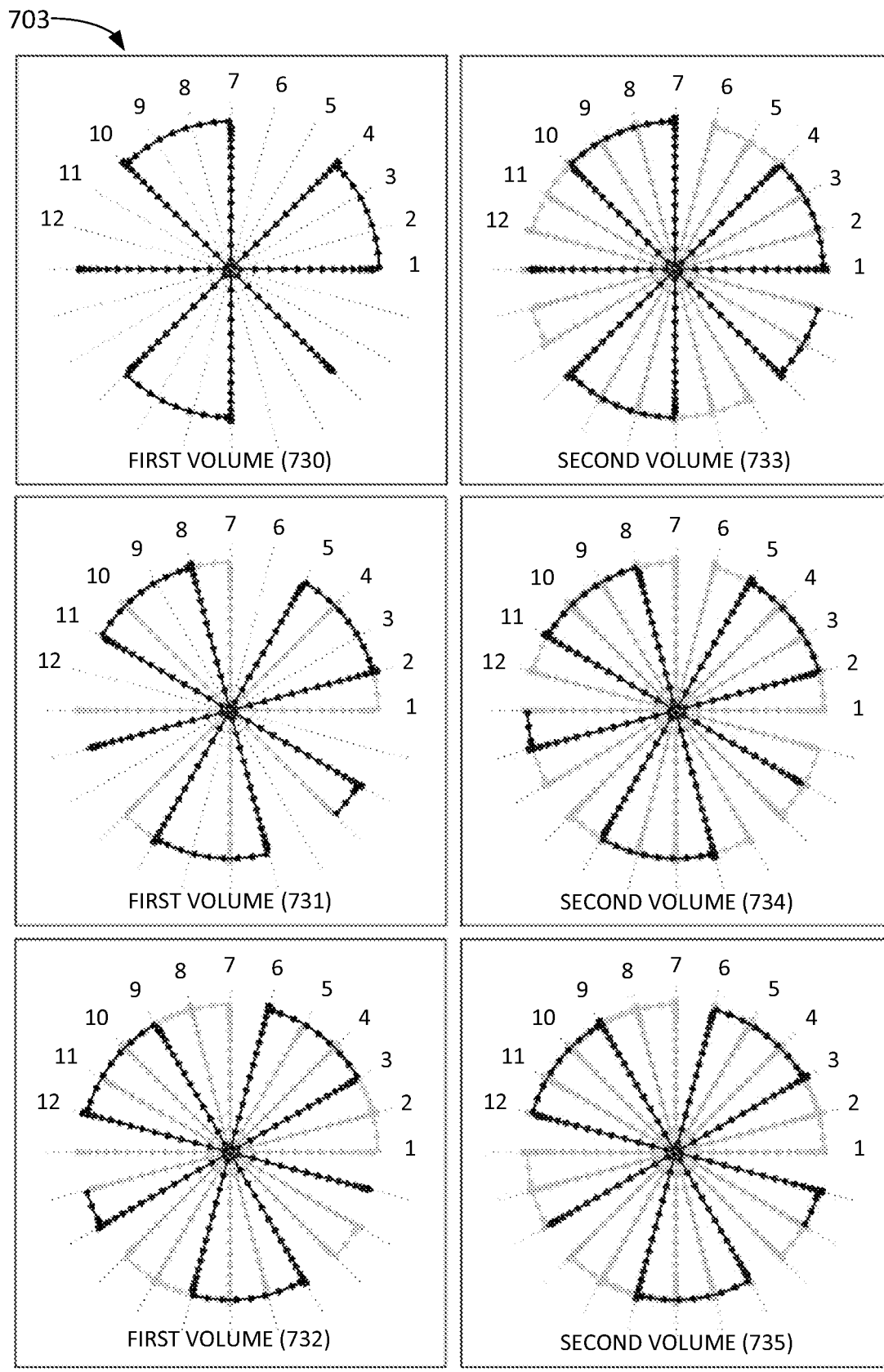
Figure 7D:
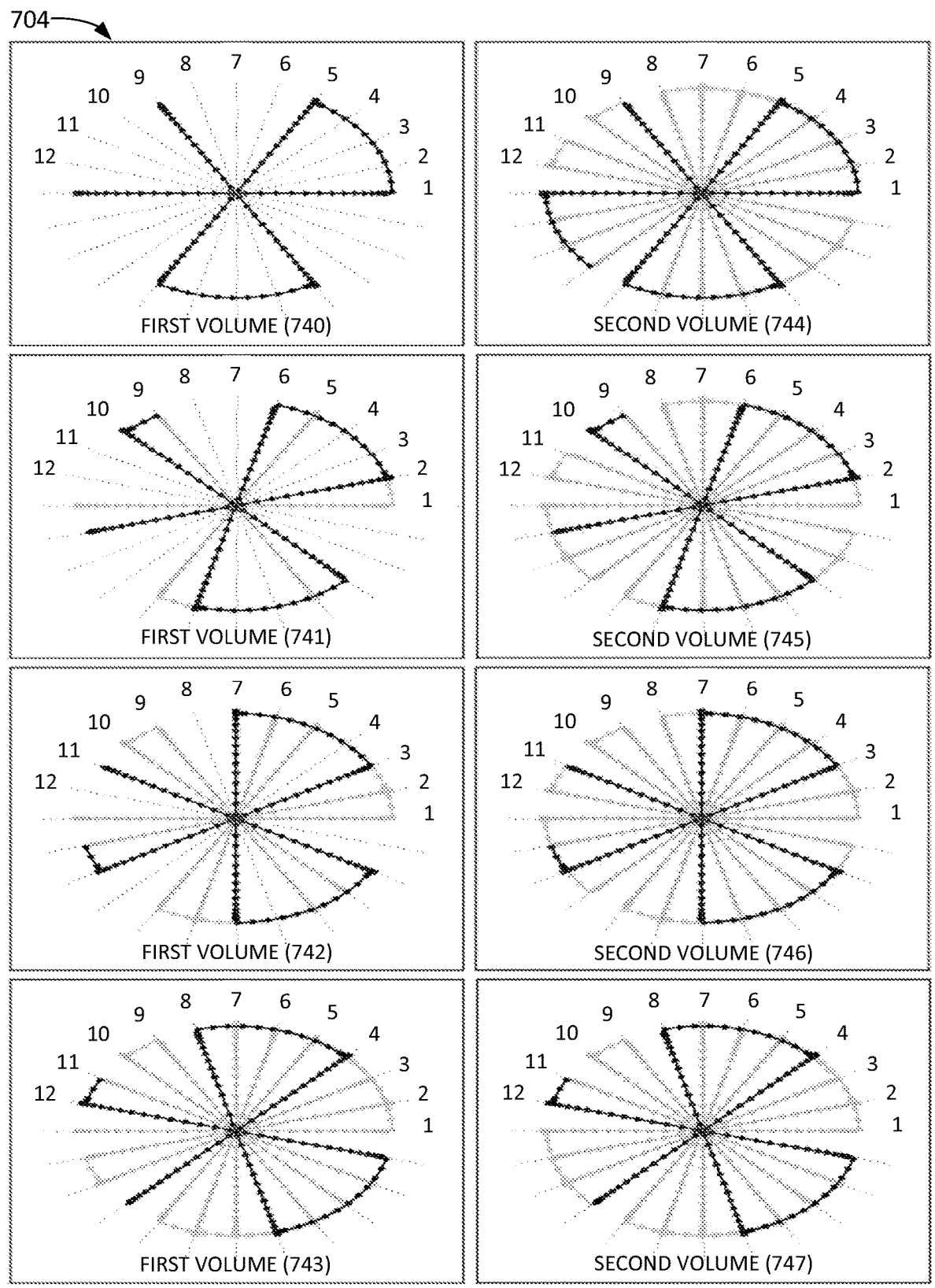

FIG. 7B illustrates a trajectory 702 of ultrasound transducer 260 for an interlaced scan based on 12 planes and an interlacing factor of two for first volume scan (items 720 and 722) and a second volume scan (items 724 and 726). FIG. 7C illustrates a trajectory 703 of ultrasound transducer for an interlaced scan based on 12 planes and an interlacing factor of 3 for first volume scan (items 730, 731, and 732) and a second volume scan (items 733, 734, and 735). FIG. 7D illustrates a trajectory 704 of ultrasound transducer for an interlaced scan based on 12 planes and an interlacing factor of four for first volume scan (items 740, 741, 742, and 743) and a second volume scan (items 744, 745, 746, and 747).

Figure 8A:
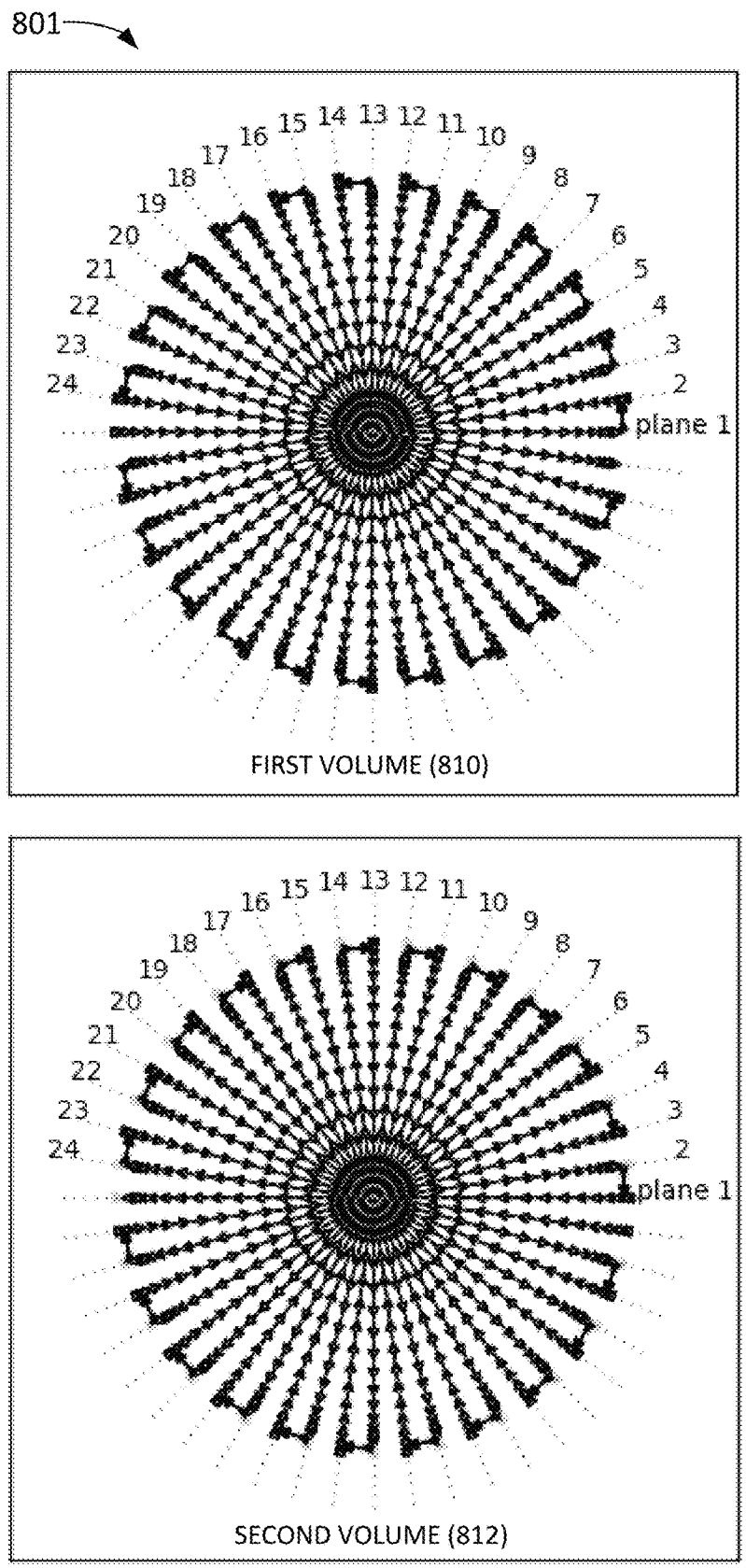
FIGS. 8A, 8B, 8C, and 8D are diagrams of exemplary ultrasound transducer trajectories for volume scans based on 24 planes according to an implementation described herein.
Figure 8B:
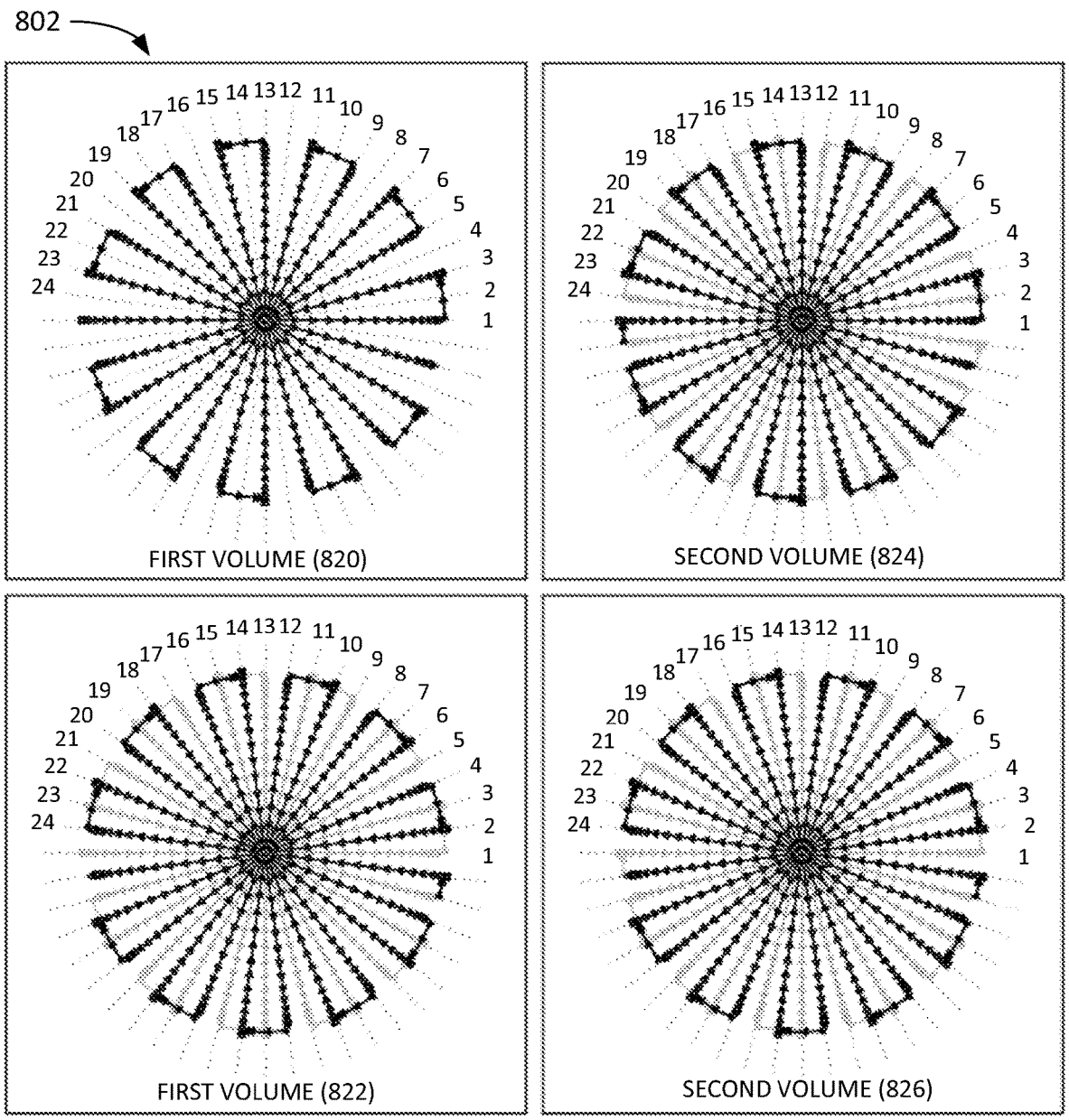
Figure 8C:
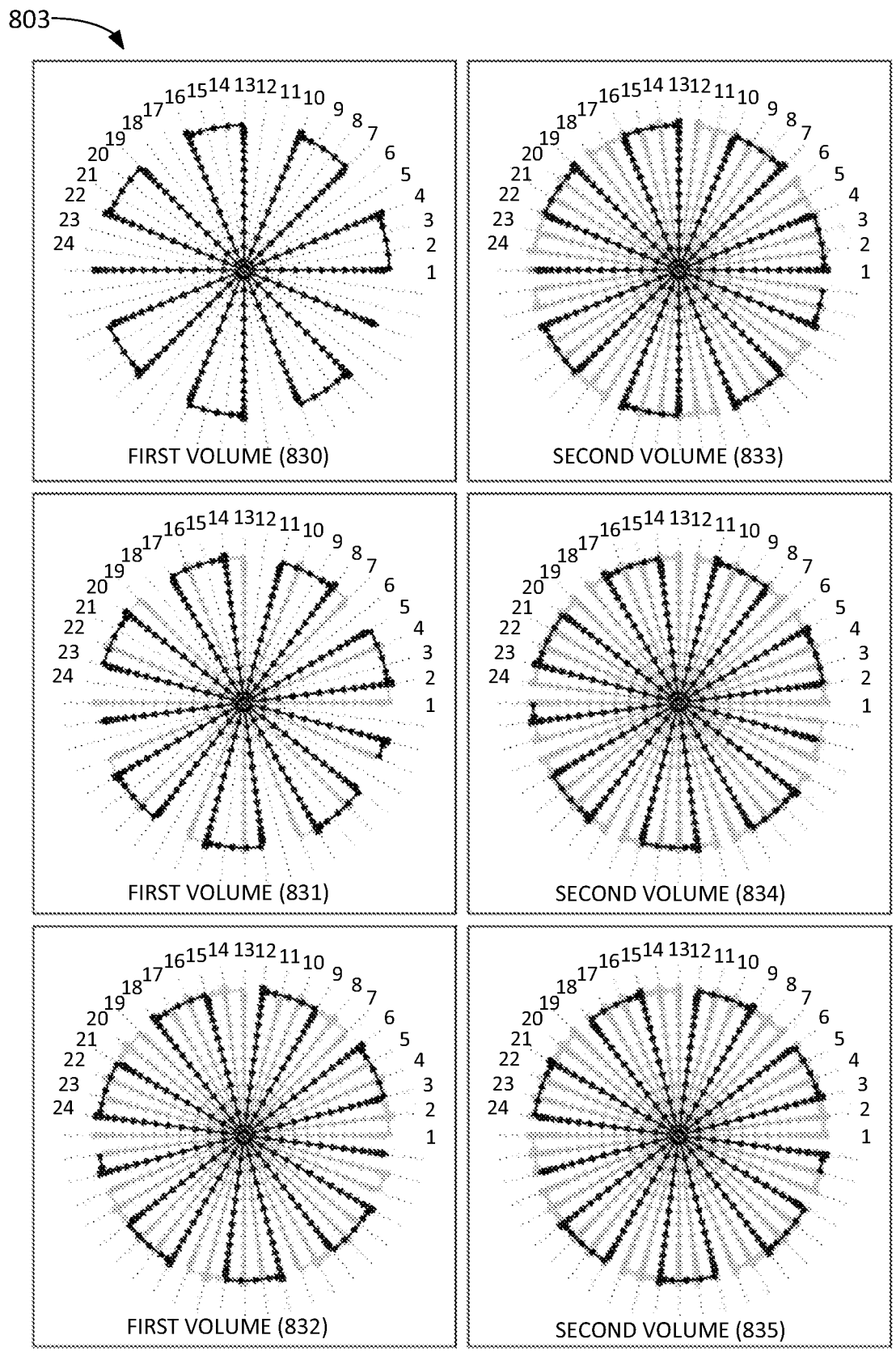
Figure 8D:
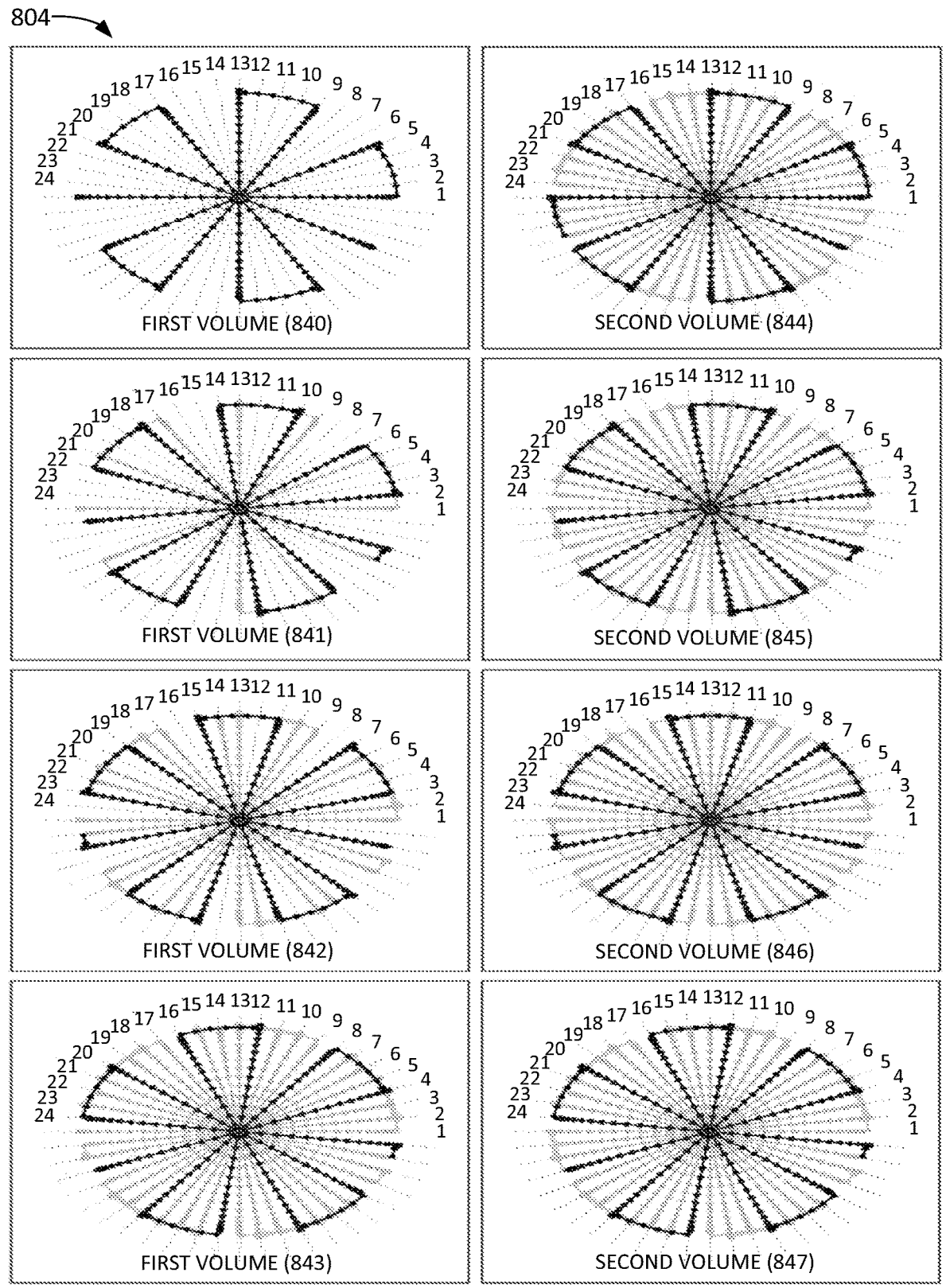

FIGS. 8A, 8B, 8C, and 8D are diagrams of exemplary ultrasound transducer trajectories for volume scans based on 24 planes. FIG. 8A illustrates a trajectory 801 of ultrasound transducer 260 for an interlaced scan based on 24 planes and an interlacing factor of one for a first volume scan 810 and a second volume scan 812. FIG. 8B illustrates a trajectory 802 of ultrasound transducer 260 for an interlaced scan based on 24 planes and an interlacing factor of two for a first volume scan (items 820 and 822) and a second volume scan (items 824 and 826). FIG. 8C illustrates a trajectory 803 of ultrasound transducer for an interlaced scan based on 24 planes and an interlacing factor of 3 for first volume scan (items 830, 831, and 832) and a second volume scan (items 833, 834, and 835). FIG. 8D illustrates a trajectory 804 of ultrasound transducer for an interlaced scan based on 24 planes and an interlacing factor of 4 for first volume scan (items 840, 841, 842, and 843) and a second volume scan (items 844, 845, 846, and 847).

Figure 9A:
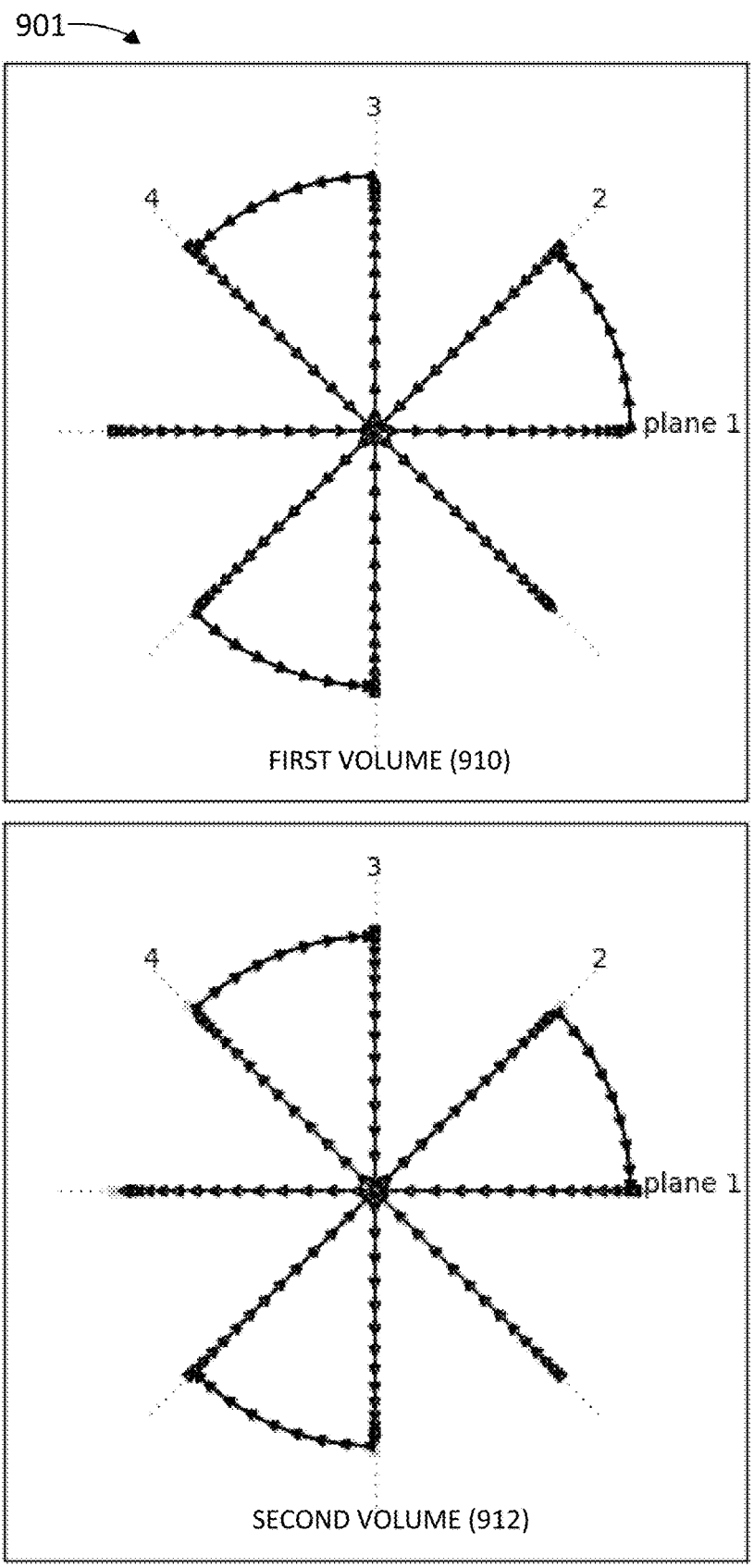
FIGS. 9A and 9B are diagrams of exemplary ultrasound transducer trajectories for volume scans based on four planes according to an implementation described herein.
Figure 9B:
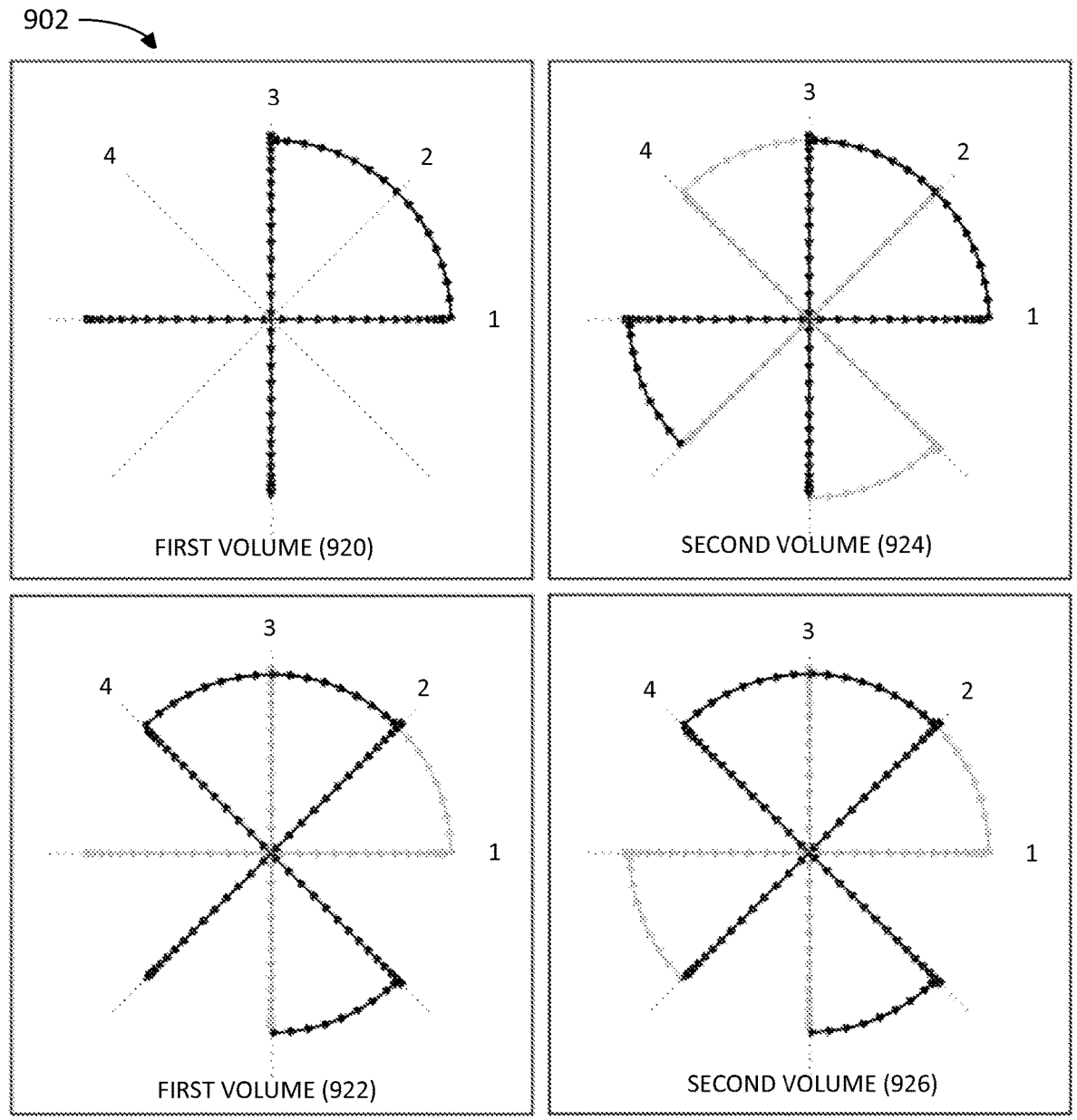

FIGS. 9A and 9B are diagrams of exemplary ultrasound transducer trajectories for volume scans based on four planes. FIG. 9A illustrates a trajectory 901 of ultrasound transducer 260 for an interlaced scan based on four planes and an interlacing factor of one for a first volume scan 910 and a second volume scan 912. FIG. 9B illustrates a trajectory 902 of ultrasound transducer 260 for an interlaced scan based on four planes and an interlacing factor of two for first volume scan (items 920 and 922) and a second volume scan (items 924 and 926).

Figure 10A:
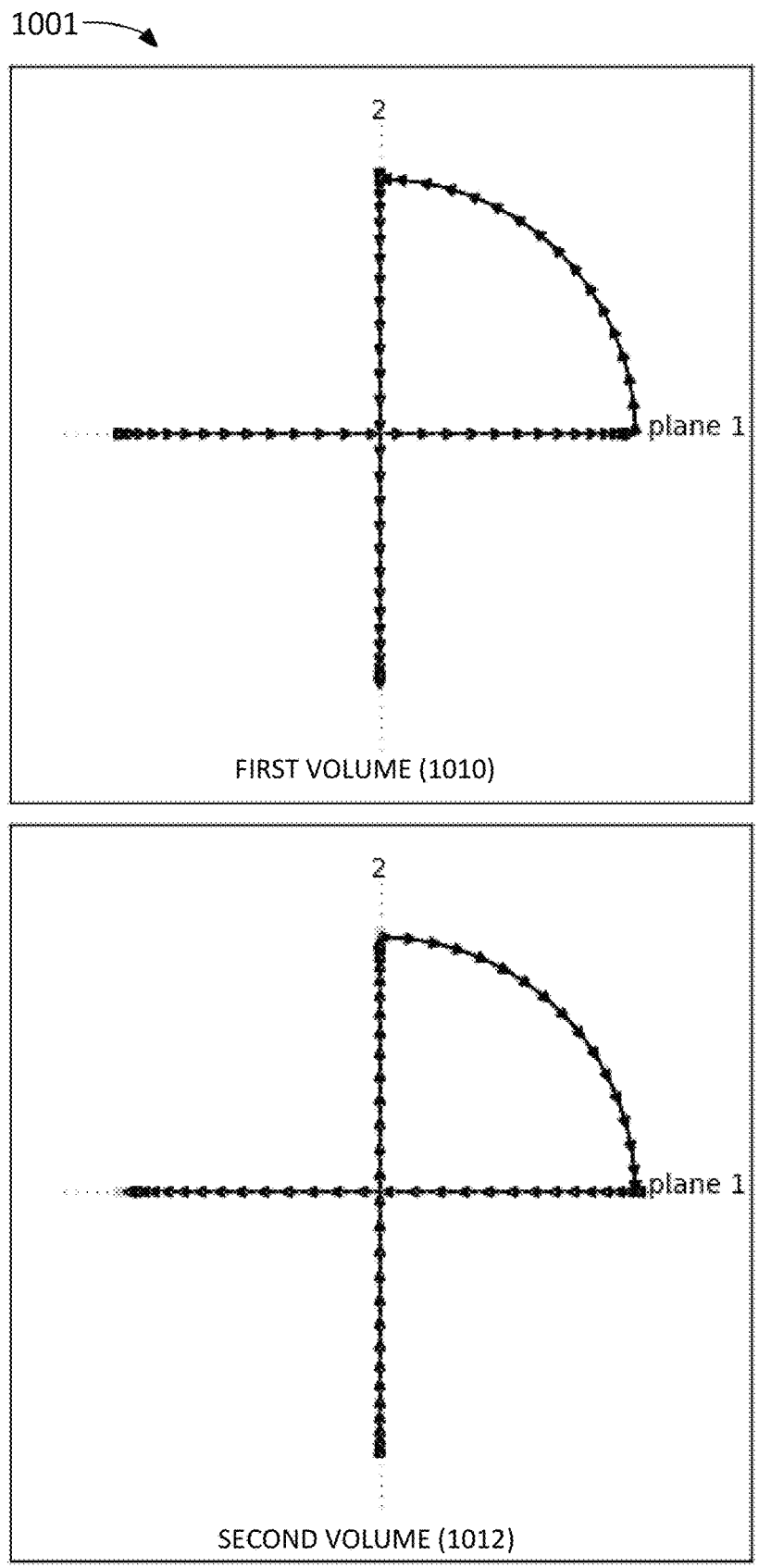
FIGS. 10A and 10B are diagrams of exemplary ultrasound transducer trajectories for volume scans based on two planes according to an implementation described herein.
Figure 10B:
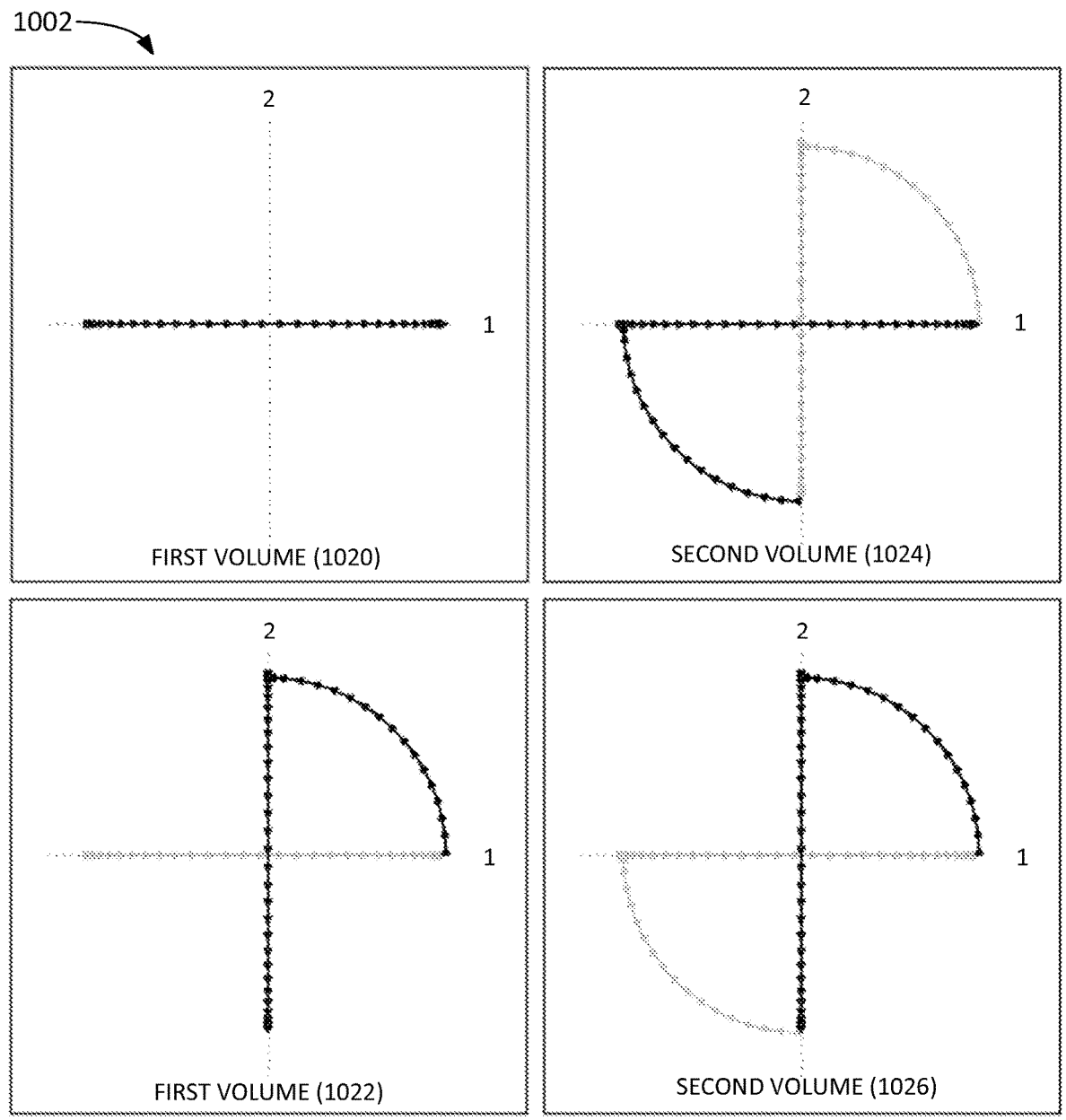

FIGS. 10A and 10B are diagrams of exemplary ultrasound transducer trajectories for volume scans based on two planes. FIG. 10A illustrates a trajectory 1001 of ultrasound transducer 260 for an interlaced scan based on two planes and an interlacing factor of one for first bi-plane scan 1010 and a second bi-plane scan 1012. FIG. 10B illustrates a trajectory 1002 of ultrasound transducer 260 for an interlaced scan based on two planes and an interlacing factor of two for first bi-plane scan (items 1020 and 1022) and a second bi-plane scan (items 1024 and 1026). An interlaced scan based on 2 planes and an interlacing factor of two corresponds to the case of continuous bi-plane scanning.

Figure 11:
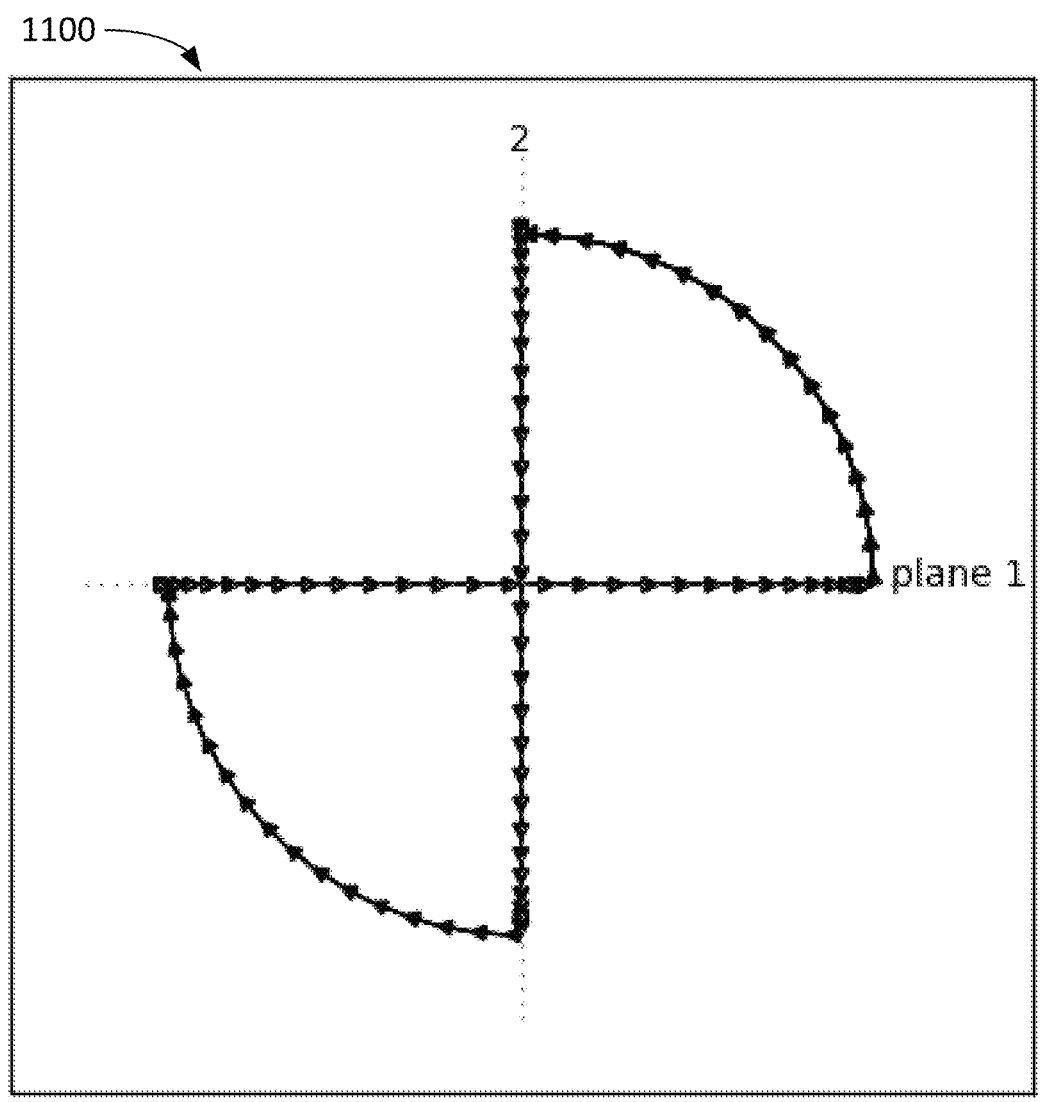
FIG. 11 is a diagram of an exemplary ultrasound transducer trajectory for continuous bi-plane scanning according to an implementation described herein.

FIG. 11 illustrates a continuous bi-plane scanning trajectory 1100. In continuous bi-plane scanning, ultrasound transducer 260 may collect two orthogonal ultrasound images (e.g., B-mode images). If the speed of phi motor 240 and theta motor 220 is sufficiently fast, continuous bi-plane scanning may be used for real-time, or near real-time, bi-plane ultrasound imaging. Continuous bi-plane scanning may be useful, for example, for obtaining a real-time transverse and longitudinal view of an area of interest in a patient's body.

FIGS. 7A, 7B, 7C, and 7D; 8A, 8B, 8C, and 8D; 9A and 9B; 10A and 10B; and 11 illustrate ultrasound transducer trajectories for volume scans using ultrasound probe 110 of FIG. 2A, which includes movement of theta motor 220 and phi motor 240. However, the illustrated ultrasound transducer trajectories may also be applied for volume scans using ultrasound probe 110 of FIG. 2B with theta motor 220 and 1D transducer array 275, if phi motor movement 714 is replaced with an electronically controlled scan using 1D transducer array 275, which does not include any physical motor movement but rather represents the particular plane being scanned. Thus, in such implementations, the arrows representing the direction of phi motor movement 714 in each plane may be ignored.

Figure 12:
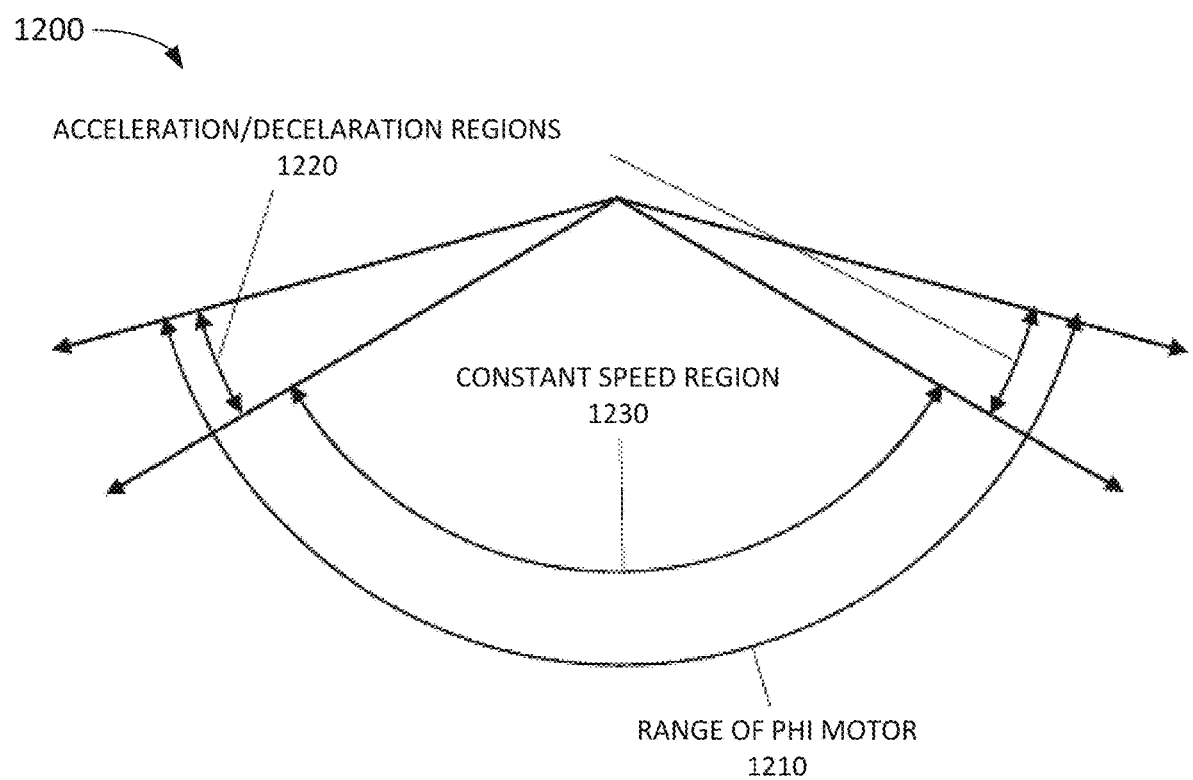
FIG. 12 is a diagram illustrating the range of motion of a phi motor of an ultrasound probe according to an implementation described herein.

FIG. 12 is a diagram 1200 of the range of motion of phi motor 240. As shown in FIG. 12, a range of motion 1210 for phi motor 240 may include a sector of a circle. For example, in some implementations, range of motion 1210 may span less than 180°, such as approximately 150°. Range of motion 1210 may include two acceleration/deceleration regions 1220 and a constant speed region 1230. For example, in some implementations, constant speed region 1230 may span approximately 120°. When phi motor 240 scans a plane, phi motor 240 may accelerate from a rotation speed of zero to a scanning motor speed, and the scanning motor speed may be reached by the time phi motor 240 arrives at the beginning of constant speed region 1230. Ultrasound transducer 260 may then initiate scanning the plane and may continue to scan the plane as phi motor 240 moves across constant speed region 1230. Ultrasound transducer 260 may stop scanning at the end of constant speed region 1230 and phi motor 240 may start to decelerate, reaching a stationary position at the end of acceleration/deceleration region 1220, which also corresponds to the end of range of motion 1210. Thus, phi motor 240 may scan a sector corresponding to constant speed region 1230 and resulting in an ultrasound image with a viewing angle corresponding to the angle of constant speed region 1230 (e.g., 120°).

As explained above with respect to FIG. 12, no scanning takes place in acceleration/deceleration regions 1220. Therefore, a volume scan speed may be improved by taking advantage of the time phi motor 240 is moving through one of the acceleration/deceleration regions 1220 by moving theta motor 220 from a previous plane (during acceleration) or to a next plane (during deceleration) of the interlaced scan. Thus, the movement of theta motor 220 and phi motor 240 may overlap.

Figure 13A:
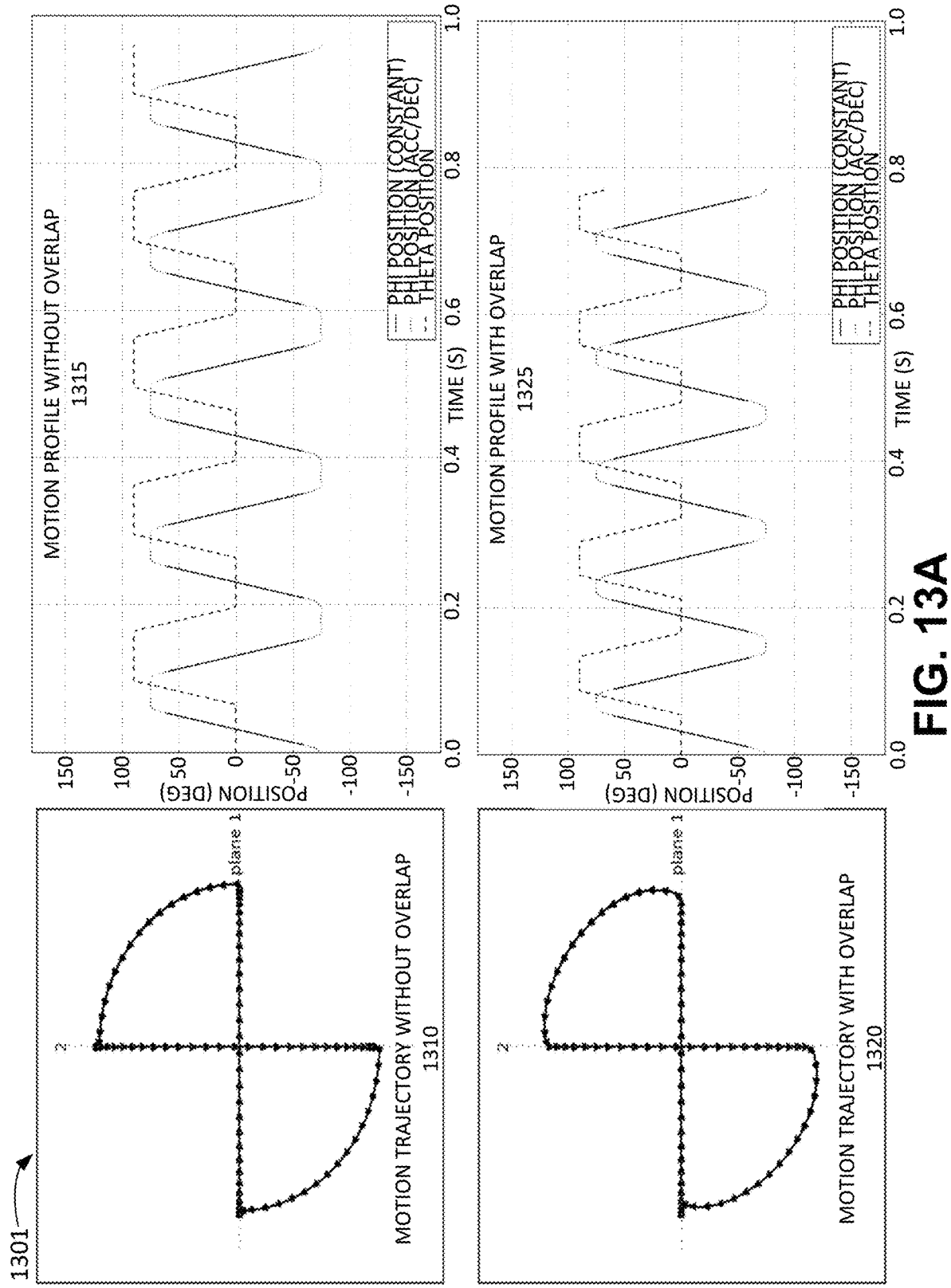
FIG. 13A is a diagram illustrating the motion trajectories and positions of motors for a two plane volume scan without overlap and with overlap according to an implementation described herein.

FIG. 13A is a diagram 1301 illustrating the motion trajectories and positions of motors for a two plane volume scan without overlap and with overlap. As shown in FIG. 13A, a motion trajectory without overlap 1310 results in motion profile without overlap 1315, which is shown in FIG. 13A for five consecutive volume scans. Also shown in FIG. 13A is a motion trajectory with overlap 1320, which results in motion profile with overlap 1325, also shown for five consecutive volume scans. With overlap, theta motor 220 starts to move to the next plane while phi motor 240 is decelerating and phi motor 240 starts to accelerate for the scan of the next plane while theta motor 220 is still moving and before theta motor 220 completes the movement to the next plane. Motion profile with overlap 1325 illustrates that in this exemplary interlaced scan, overlap yields a time savings of, for example, greater than 0.2 seconds for five volume scans, resulting in faster volume scans closer to real-time and reduced motion blur.

Figure 13B:
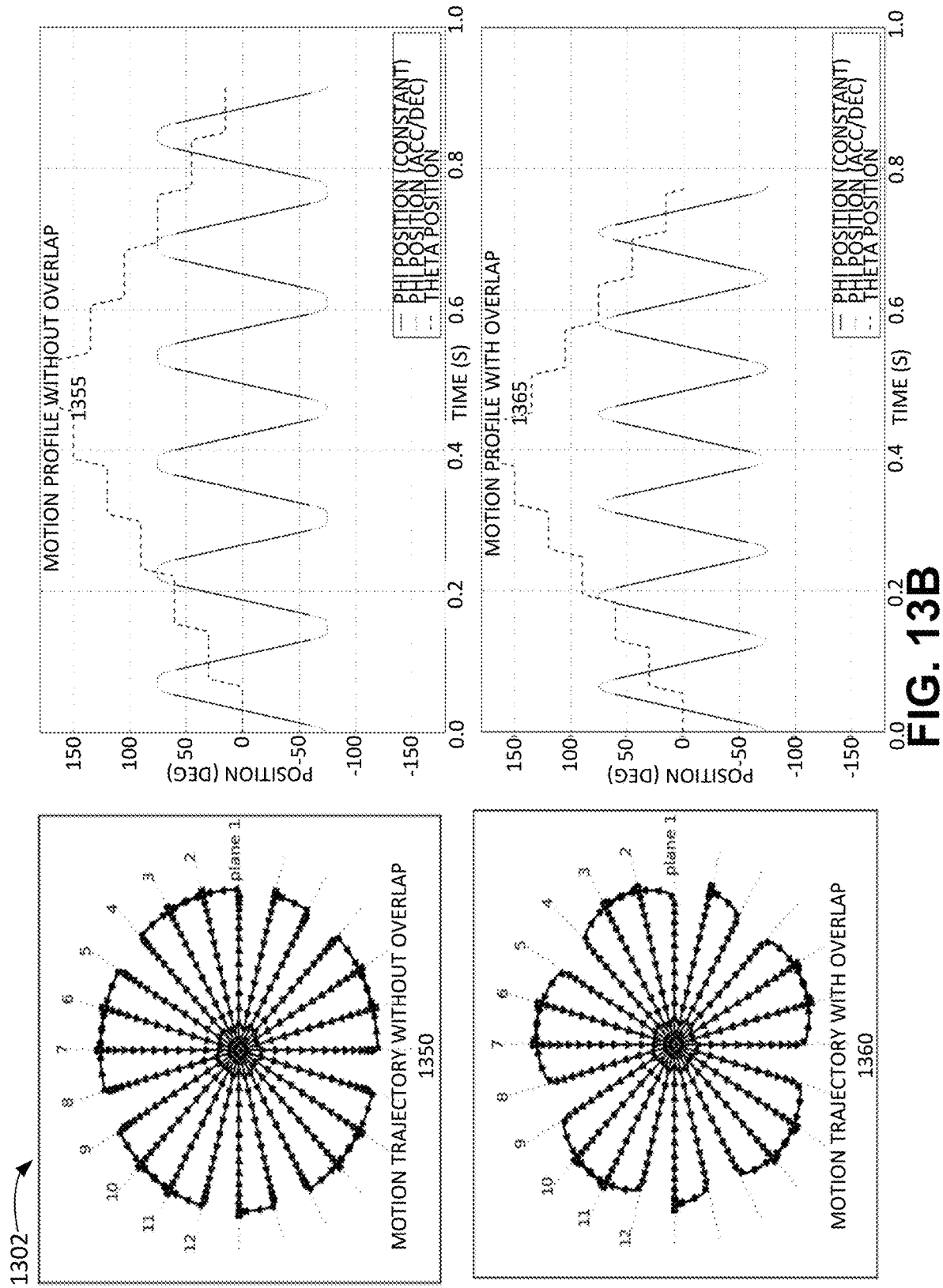
FIG. 13B is a diagram illustrating the motion trajectories and positions of motors for a 12 plane volume scan without overlap and with overlap according to an implementation described herein.

FIG. 13B is a diagram illustrating the motion trajectories and positions of motors for a 12 plane volume scan without overlap and with overlap. As shown in FIG. 13B, a motion trajectory without overlap 1350 results in motion profile without overlap 1355, which is shown in FIG. 13B for one volume scan. Also shown in FIG. 13B is a motion trajectory with overlap 1360, which results in motion profile with overlap 1365, also shown for one volume scan. Motion profile with overlap 1365 illustrates that in this exemplary interlaced scan with 12 scan planes, overlap yields a time savings of, for example, greater than 0.2 seconds for a single volume scan.

As explained above with reference to FIG. 2, in some implementations, ultrasound probe 110 may be configured to enable continuous motion of theta motor 220 in one direction. Continuous motion of theta motor 220 may be enabled by, for example, replacing wiring to ultrasound transducer 260 with a conductive slip ring and/or a wireless connection. FIGS. 14A and 14B are diagrams of exemplary scanning order tables with continuous theta motor movement. In implementations with continuous motion of theta motor 220, the rules for an interlaced scan may be replaced with the following rules: the direction of phi motor 240 changed with every plane during a volume scan and the direction of theta motor 220 does not change.

FIG. 14A illustrates a scanning order table 1401 for an interlacing scan with 12 planes, an interlacing factor k of 2, and continuous motion of theta motor 220. As shown in FIG. 14A, the direction of phi motor 240 changes with each plane and the direction of theta motor 220 does not change. FIG. 14B illustrates a scanning order table 1402 for an interlacing scan with 12 planes, an interlacing factor k of four, and continuous motion of theta motor 220. As shown in FIG. 14B, the direction of phi motor 240 changes with each plane and the direction of theta motor 220 does not change.

Figure 15A:
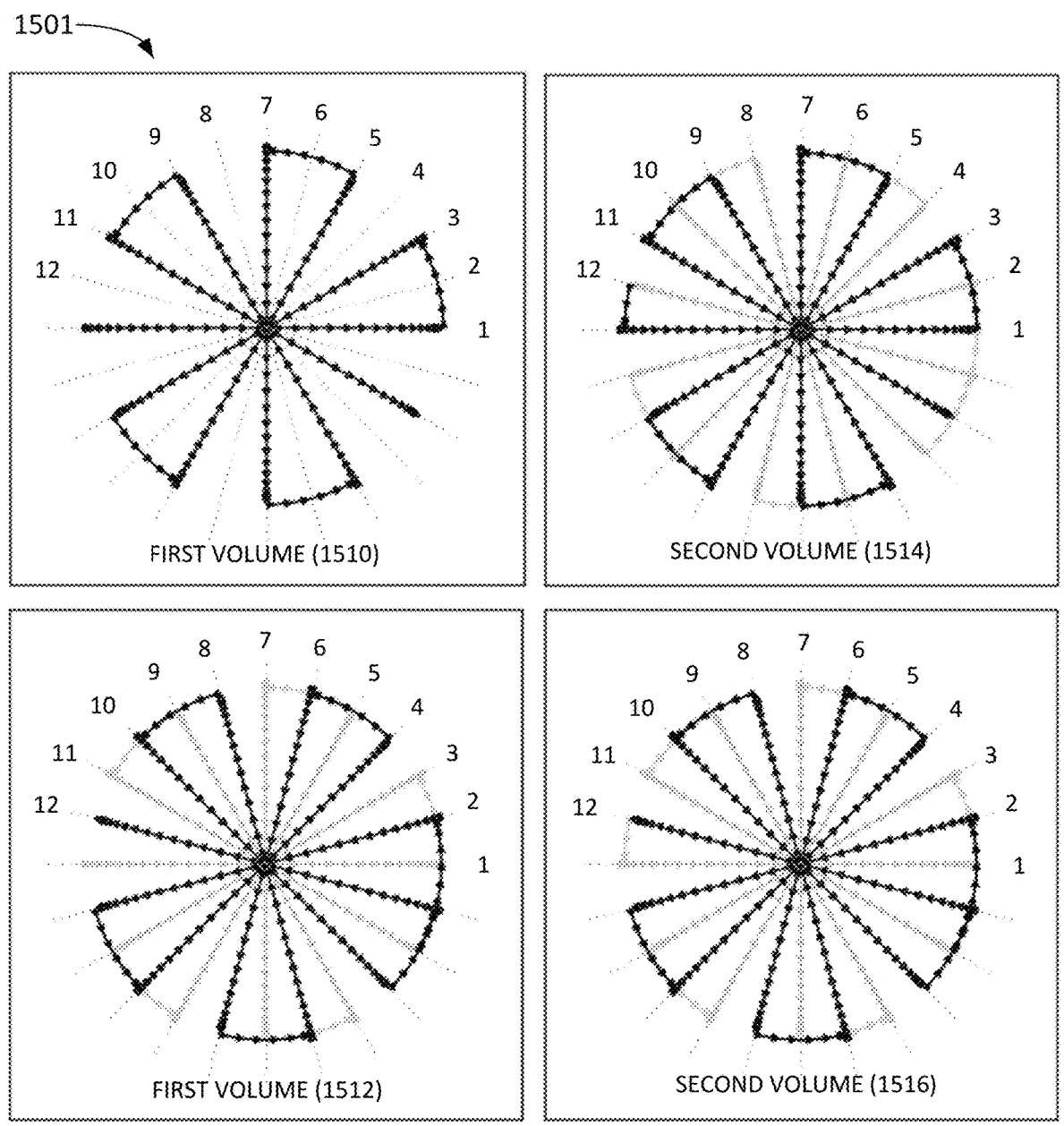
FIGS. 15A, 15B, and 15C are diagrams of exemplary ultrasound transducer trajectories for volume scans based on 12 planes with continuous theta motor movement according to an implementation described herein.
Figure 15B:
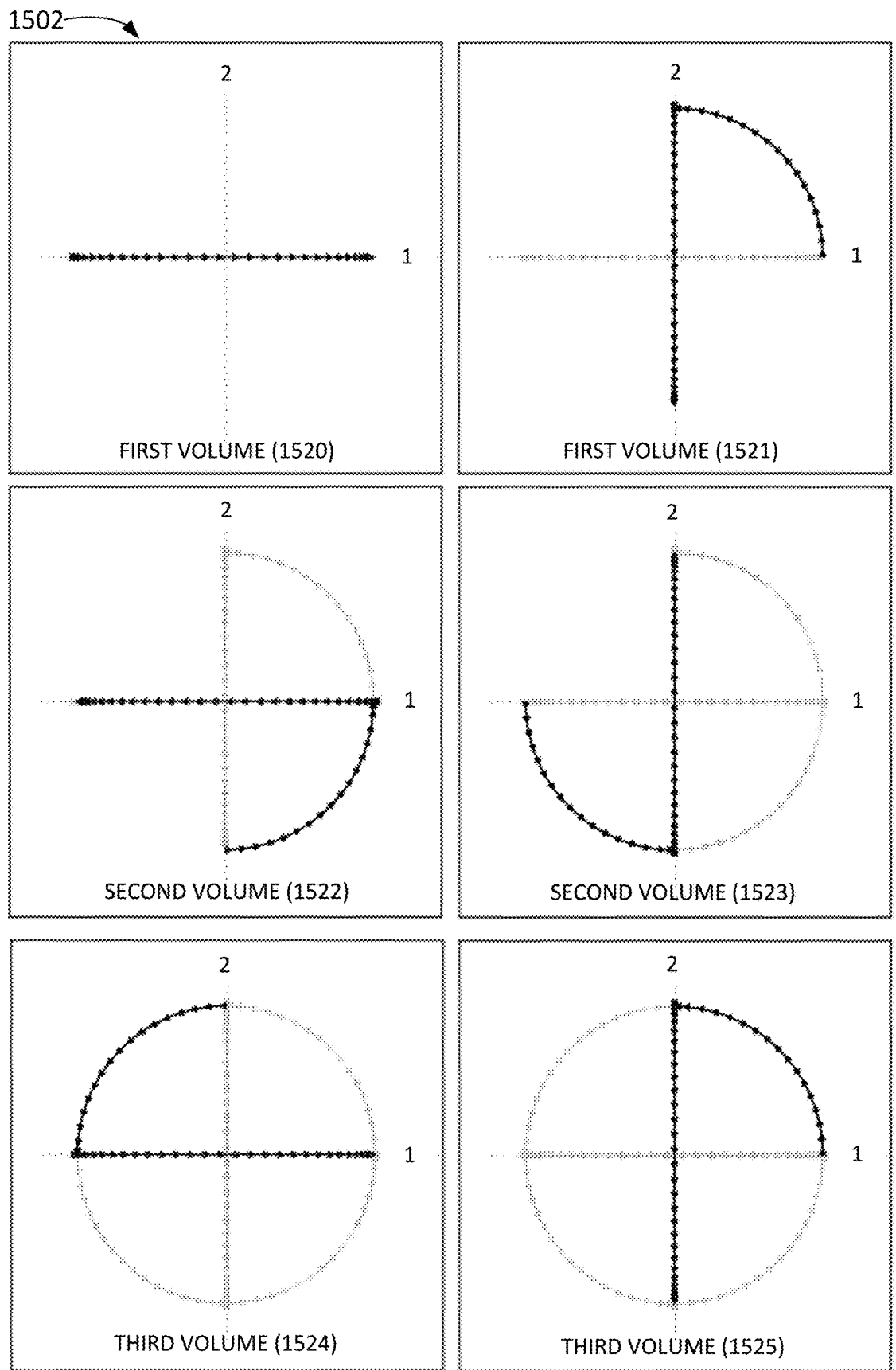
Figure 15C:
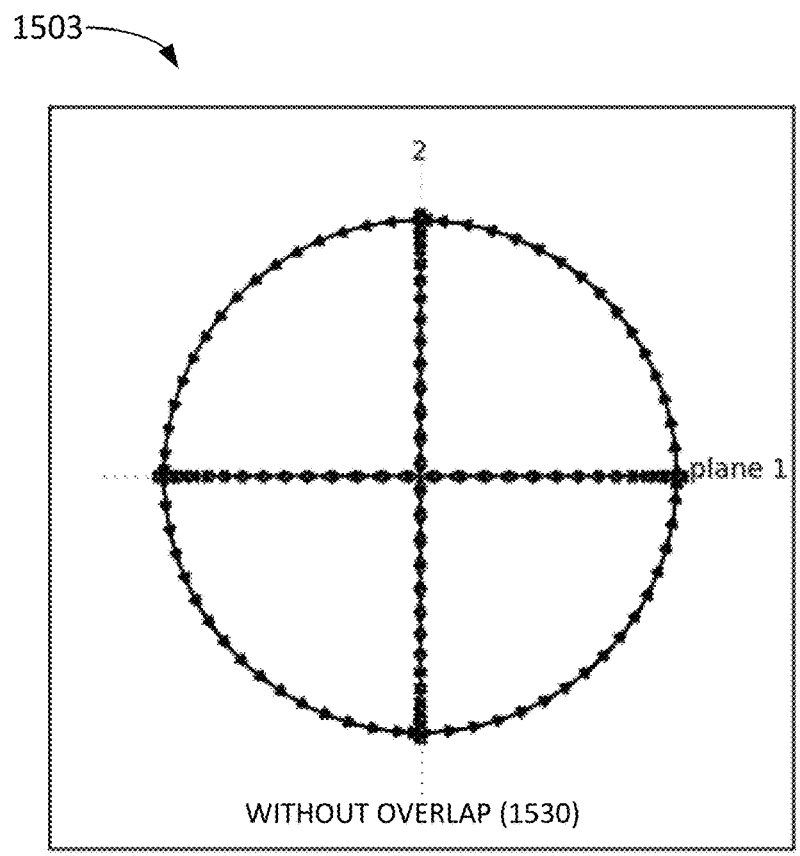
Figure 15C:
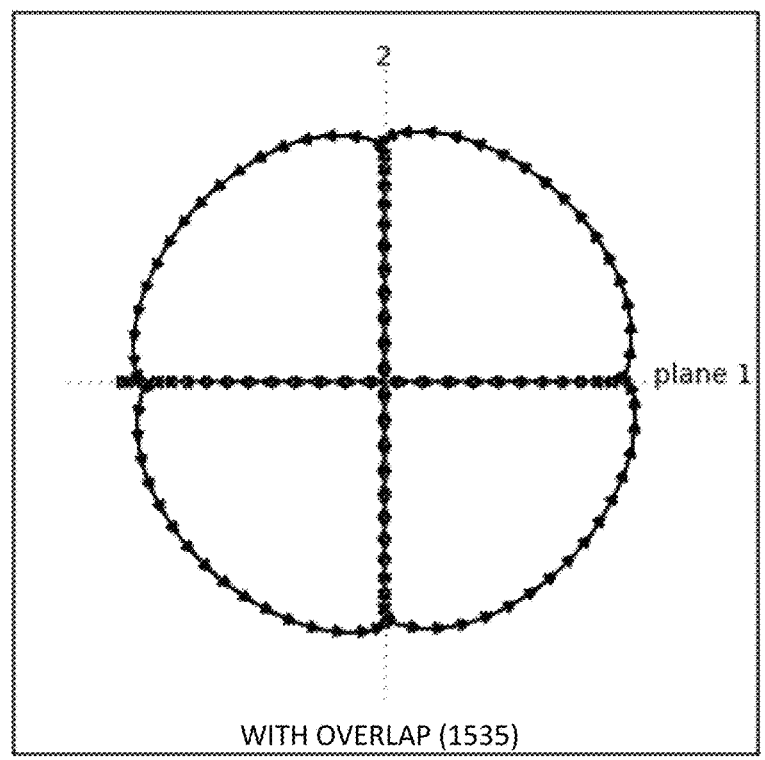

FIGS. 15A, 15B, and 15C are diagrams of exemplary ultrasound transducer trajectories for volume scans based on 12 planes with continuous theta motor movement. FIG. 15A illustrates a trajectory 1501 of ultrasound transducer 260 for an interlaced scan based on 12 planes and an interlacing factor of two for first volume scan (items 1510 and 1512) and a second volume scan (items 1514 and 1516). FIG. 15B illustrates a trajectory 1502 of ultrasound transducer for an interlaced scan based on two planes and an interlacing factor of two (i.e., a bi-plane scan) for first volume scan (items 1520 and 1521), a second volume scan (items 1522 and 1523), and a third volume scan (items 1524 and 1525). FIG. 15C illustrates a diagram 1503 comparing trajectories of ultrasound transducer 260 for continuous bi-plane scanning with continuous theta motor movement without overlap (1530) and with overlap (item 1535).

In the preceding specification, various preferred embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded in an illustrative rather than restrictive sense.

For example, while a series of blocks have been described with respect to FIG. 5, the order of the blocks may be modified in other implementations. Further, non-dependent blocks may be performed in parallel.

Although embodiments described above refer to scanning a bladder, other organs, joints, vessels, and/or body areas, such as an aorta, prostate, kidney, uterus, ovaries, heart, etc., could scanned and/or imaged in other implementations. Furthermore, in some implementations, selection of the number of planes and/or the interlacing factor may be automatic based on a size of an image, the area of interest, and/or another parameter.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

The term "logic," as used herein, may refer to a combination of one or more processors configured to execute instructions stored in one or more memory devices, may refer to hardwired circuitry, and/or may refer to a combination thereof. Furthermore, a logic may be included in a single device or may be distributed across multiple, and possibly remote, devices.

For the purposes of describing and defining the present invention, it is additionally noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

No element, act, or instruction used in the present application should be construed as critical or essential to the embodiments unless explicitly described as such. Also, as used herein, the article "a" is intended to include one or more items. Further, the phrase "based on" is intended to mean "based, at least in part, on" unless explicitly stated otherwise.

What is claimed is:

1. A method performed by a device, the method comprising:
   selecting, by the device, a number of intersecting scan planes for an interlacing scan to scan a volume of an area of interest in a patient's body using an ultrasound transducer;
   selecting, by the device, an interlacing factor for the interlacing scan;
   dividing, by the device, the scan planes into a plurality of groups of scan planes based on the interlacing factor; and
   performing, by the device, the interlacing scan by controlling a first motor configured to rotate the ultrasound transducer around a transverse axis of the ultrasound transducer to scan a plane and a second motor configured to rotate the ultrasound transducer around a longitudinal axis of the ultrasound transducer to move to a different plane, and wherein the first motor rotates in a first direction for at least some of the scan planes and in a second direction, opposite to the first direction, for other ones of the scan planes, and wherein the second motor rotates the ultrasound transducer in a third direction for at least one of the plurality of groups of scan planes, and rotates the ultrasound transducer in a fourth direction, opposite to the third direction, for at least one other of the plurality of groups of scan planes.

2. The method of claim 1, wherein the first motor changes rotation direction every plane and wherein the second motor changes rotation direction every group without changing rotation direction within a group.

3. The method of claim 1, wherein the scan planes are separated by an angle corresponding to one hundred and eighty degrees divided by the number of scan planes.

4. The method of claim 1, wherein dividing the scan planes into groups of scan planes based on the interlacing factor includes:
   sequentially numbering the scan planes;
   dividing the scan planes into a number of groups of scan planes corresponding to the interlacing factor; and
   sequentially distributing the numbered scan planes into the groups of scan planes.

5. The method of claim 1, wherein performing the interlacing scan includes:
   scanning a particular plane by rotating the first motor in a direction that is opposite to a direction the first motor rotated when scanning a previous plane; and
   moving to a next plane by rotating the second motor by a number of planes corresponding to the interlacing factor, wherein the direction of the second motor changes if the next plane is in a different one of the groups of scan planes than the previous plane.

6. The method of claim 1, wherein the number of scan planes corresponds to two, wherein the interlacing factor corresponds to two, and wherein performing the interlacing scan includes:
   performing continuous bi-plane scanning.

7. The method of claim 1, wherein a range of motion of the first motor includes an acceleration or deceleration region and a constant speed region, and wherein performing the interlacing scan includes:
   controlling the second motor to rotate while the first motor is in the acceleration or deceleration region of the range of motion.

8. The method of claim 7, wherein the second motor moves the ultrasound transducer from a first plane to a second plane while the first motor is in the acceleration or deceleration region of the range of motion.

9. The method of claim 1, wherein the second motor rotates in a same direction for all the groups of scan planes.

10. The method of claim 1, wherein performing the interlacing scan includes:
    performing a first volume scan with the second motor starting in a first plane; and
    performing a second volume scan with the second motor starting in a second plane, wherein the second plane is different from the first plane.

11. A system comprising:
    an ultrasound probe comprising:
      an ultrasound transducer;
      a first motor configured to rotate the ultrasound transducer around a transverse axis of the ultrasound transducer to scan a plane; and
      a second motor configured to rotate the ultrasound transducer around a longitudinal axis of the ultrasound transducer, or around another transverse axis perpendicular to the transverse axis of the first motor, to move to a different plane; and
    a controller unit configured to:
      select a number of intersecting scan planes for an interlacing scan to scan a volume of an area of interest in a patient's body using the ultrasound probe;
      select an interlacing factor for the interlacing scan;
      divide the scan planes into a plurality of groups of scan planes based on the interlacing factor; and
      perform the interlacing scan by controlling the first motor and the second motor, and wherein the first motor rotates in a first direction for at least some of the scan planes and in a second direction, opposite to the first direction, for other ones of the scan planes, and wherein the second motor rotates the ultrasound transducer in a third direction for at least one of the plurality of groups of scan planes, and rotates the ultrasound transducer in a fourth direction, opposite to the third direction, for at least one other of the plurality of groups of scan planes.

12. The system of claim 11, wherein the first motor changes rotation direction every plane and wherein the second motor changes rotation direction every group without changing rotation direction within a group.

13. The system of claim 11, wherein, when performing the interlacing scan, the controller unit is further configured to:
scan a particular plane by rotating the first motor in a direction that is opposite to a direction the first motor rotated when scanning a previous plane; and
move to a next plane by rotating the second motor by a number of planes corresponding to the interlacing factor, wherein the direction of the second motor changes if the next plane is in a different one of the groups of scan planes than the previous plane.

14. The system of claim 11, wherein the number of scan planes corresponds to two, wherein the interlacing factor corresponds to two, and wherein, when performing the interlacing scan the controller unit is further configured to:
perform continuous bi-plane scanning.

15. The system of claim 11, wherein a range of motion of the first motor includes an acceleration or deceleration region and a constant speed region, and wherein, when performing the interlacing scan the controller unit is further configured to:
control the second motor to rotate while the first motor is in the acceleration or deceleration region of the range of motion.

16. The system of claim 15, wherein the controller unit is further configured to:
control the second motor to move from a first plane to a second plane while the first motor is in the acceleration or deceleration region of the range of motion.

17. The system of claim 11, wherein the controller unit is further configured to:
control the second motor to move in a same direction for all the groups of scan planes.

18. The system of claim 11, wherein the second motor is configured to rotate the ultrasound transducer around the vertical axis.

19. The system of claim 11, wherein the second motor is configured to rotate the ultrasound transducer around the other horizontal axis perpendicular to the horizontal axis of the first motor.

20. A device comprising:
a memory storing instructions; and
a processor configured to execute the instructions to:
select a number of intersecting scan planes for an interlacing scan to scan a volume of an area of interest in a patient's body using an ultrasound transducer array;
select an interlacing factor for the interlacing scan;
divide the scan planes into a plurality of groups of scan planes based on the interlacing factor; and
perform the interlacing scan by controlling the ultrasound transducer array to scan a plane and controlling a motor configured to rotate the ultrasound transducer array around a longitudinal axis of the ultrasound transducer array to move to a different plane, and wherein the motor changes directions for every group of scan planes, of the plurality of groups of scan planes, without changing directions within a group of scan planes.

* * * * *